US010537717B2

(12) United States Patent
Terliuc et al.

(10) Patent No.: US 10,537,717 B2
(45) Date of Patent: Jan. 21, 2020

(54) ENDOSCOPY DEVICES AND APPLICATIONS THEREOF

(71) Applicant: SMART MEDICAL SYSTEMS LTD., Raanana (IL)

(72) Inventors: Gad Terliuc, Raanana (IL); Gilad Luria, Givatai'Im (IL)

(73) Assignee: SMART MEDICAL SYSTEMS LTD, Raanana (IL)

( * ) Notice: Subject to any disclaimer, the term of this patent is extended or adjusted under 35 U.S.C. 154(b) by 438 days.

(21) Appl. No.: 14/439,235

(22) PCT Filed: Oct. 31, 2013

(86) PCT No.: PCT/IL2013/050894
§ 371 (c)(1),
(2) Date: Apr. 29, 2015

(87) PCT Pub. No.: WO2014/068569
PCT Pub. Date: May 8, 2014

(65) Prior Publication Data
US 2015/0273191 A1    Oct. 1, 2015

Related U.S. Application Data

(60) Provisional application No. 61/796,099, filed on Nov. 2, 2012, provisional application No. 61/796,100, filed on Nov. 2, 2012.

(51) Int. Cl.
*A61M 25/10* (2013.01)
*A61M 25/00* (2006.01)

(52) U.S. Cl.
CPC .... *A61M 25/10184* (2013.11); *A61M 25/007* (2013.01)

(58) Field of Classification Search
CPC .............. A61B 1/00082; A61M 25/10; A61M 25/1002; A61M 25/1006; A61M 25/1018; A61M 25/10184
See application file for complete search history.

(56) References Cited

U.S. PATENT DOCUMENTS

| 4,261,339 | A | * | 4/1981 | Hanson | .............. A61M 25/0111 600/18 |
| 4,931,036 | A | | 6/1990 | Kanai | |

(Continued)

FOREIGN PATENT DOCUMENTS

| CN | 101103899 A | 1/2008 |
| CN | 102458219 A | 5/2012 |

(Continued)

OTHER PUBLICATIONS

AA_ISR_WO/2014/068569: International Search Report in WO/2014/068569 dated Apr. 24, 2014.

(Continued)

*Primary Examiner* — Sarah A Simpson
(74) *Attorney, Agent, or Firm* — Alphapatent Associates, Ltd; Daniel J. Swirsky

(57) ABSTRACT

A balloon catheter assembly including an elongate catheter tube including a lumen having a first cross sectional area, a wire extending through the lumen, and an inflatable balloon mountably associated with the tube and the wire, the tube being formed with a plurality of balloon inflation apertures communicating with the lumen, the apertures having a total aperture cross sectional area which exceeds the first cross sectional area and including at least two apertures being arranged at different azimuthal locations along the tube underlying the balloon and the balloon being characterized by an inflated state having a ratio of maximum inflated diameter to length of more than 0.4 and a corresponding deflated state wherein at least a first portion of the balloon (Continued)

is capable of being twisted relative to at least a second portion thereof, resulting in at least partial blockage of at least one but not all of the apertures.

12 Claims, 15 Drawing Sheets

(56) References Cited

U.S. PATENT DOCUMENTS

| | | | |
|---|---|---|---|
| 5,021,045 A | 6/1991 | Buckberg et al. | |
| 5,403,339 A | 4/1995 | Nobuyoshi et al. | |
| 6,544,217 B1 | 4/2003 | Gulachenski et al. | |
| 6,793,661 B2 | 9/2004 | Hamilton et al. | |
| 7,963,911 B2 | 6/2011 | Terliuc | |
| 8,172,783 B1 | 5/2012 | Ray | |
| 8,727,970 B2 | 5/2014 | Terliuc et al. | |
| 9,119,532 B2 | 9/2015 | Terliuc et al. | |
| 9,427,142 B2 | 8/2016 | Terliuc | |
| 9,596,979 B2 | 3/2017 | Terliuc et al. | |
| 9,661,994 B2 | 5/2017 | Terliuc et al. | |
| 10,052,014 B2 | 8/2018 | Terliuc et al. | |
| 2001/0016725 A1 | 8/2001 | Valley et al. | |
| 2002/0095160 A1 | 7/2002 | Bonutti | |
| 2002/0183716 A1* | 12/2002 | Herweck | A61L 29/041 604/509 |
| 2004/0176757 A1 | 9/2004 | Sinelnikov et al. | |
| 2007/0270897 A1 | 11/2007 | Skerven | |
| 2009/0018500 A1 | 1/2009 | Carter | |
| 2009/0069878 A1 | 3/2009 | Weber et al. | |
| 2009/0187069 A1 | 7/2009 | Terliuc et al. | |
| 2009/0287058 A1 | 11/2009 | Terliuc | |
| 2010/0217185 A1 | 8/2010 | Terliuc et al. | |
| 2010/0261662 A1 | 10/2010 | Schreck et al. | |
| 2011/0264039 A1 | 10/2011 | Thielen | |
| 2012/0095292 A1 | 4/2012 | Gunday | |
| 2014/0088362 A1 | 3/2014 | Terliuc et al. | |
| 2015/0273191 A1 | 10/2015 | Terliuc et al. | |
| 2015/0335229 A1 | 11/2015 | Terliuc | |
| 2016/0022120 A1 | 1/2016 | Terliuc et al. | |
| 2016/0095508 A1 | 4/2016 | Terliuc et al. | |
| 2017/0027415 A1 | 2/2017 | Terliuc et al. | |
| 2017/0027433 A1 | 2/2017 | Terliuc | |
| 2017/0100017 A1 | 4/2017 | Terliuc et al. | |
| 2017/0203080 A1 | 7/2017 | Terliuc et al. | |
| 2017/0216568 A1 | 8/2017 | Terliuc et al. | |
| 2017/0360282 A1 | 12/2017 | Terliuc et al. | |
| 2018/0084973 A1 | 3/2018 | Terliuc et al. | |
| 2018/0140175 A1 | 5/2018 | Luria et al. | |
| 2018/0333043 A1 | 11/2018 | Terliuc et al. | |

FOREIGN PATENT DOCUMENTS

| | | | |
|---|---|---|---|
| CN | 102695541 A | 9/2012 | |
| IL | 177148 A | 8/2001 | |
| JP | S63229060 | 9/1988 | |
| WO | WO1992015360 A1 | 9/1992 | |
| WO | 2005074377 | 8/2005 | |
| WO | 2007017854 | 2/2007 | |
| WO | 2007135665 | 11/2007 | |
| WO | 2008004228 | 1/2008 | |
| WO | 2008142685 | 11/2008 | |
| WO | 2009122395 | 10/2009 | |
| WO | 2010046891 | 4/2010 | |
| WO | 2010137025 | 12/2010 | |
| WO | WO-2010137025 A2 * | 12/2010 | ......... A61B 1/00082 |
| WO | 2011111040 | 9/2011 | |
| WO | 2012120492 | 9/2012 | |

OTHER PUBLICATIONS

AB_IPRP1_ WO/2014/068569: International Preliminary Report on Patentability in WO/2014/068569 dated May 5, 2015.

AC_WOSA_ WO/2014/068569: Written Opinion of the International Search Authority in WO/2014/068569 dated Apr. 24, 2014.

* cited by examiner

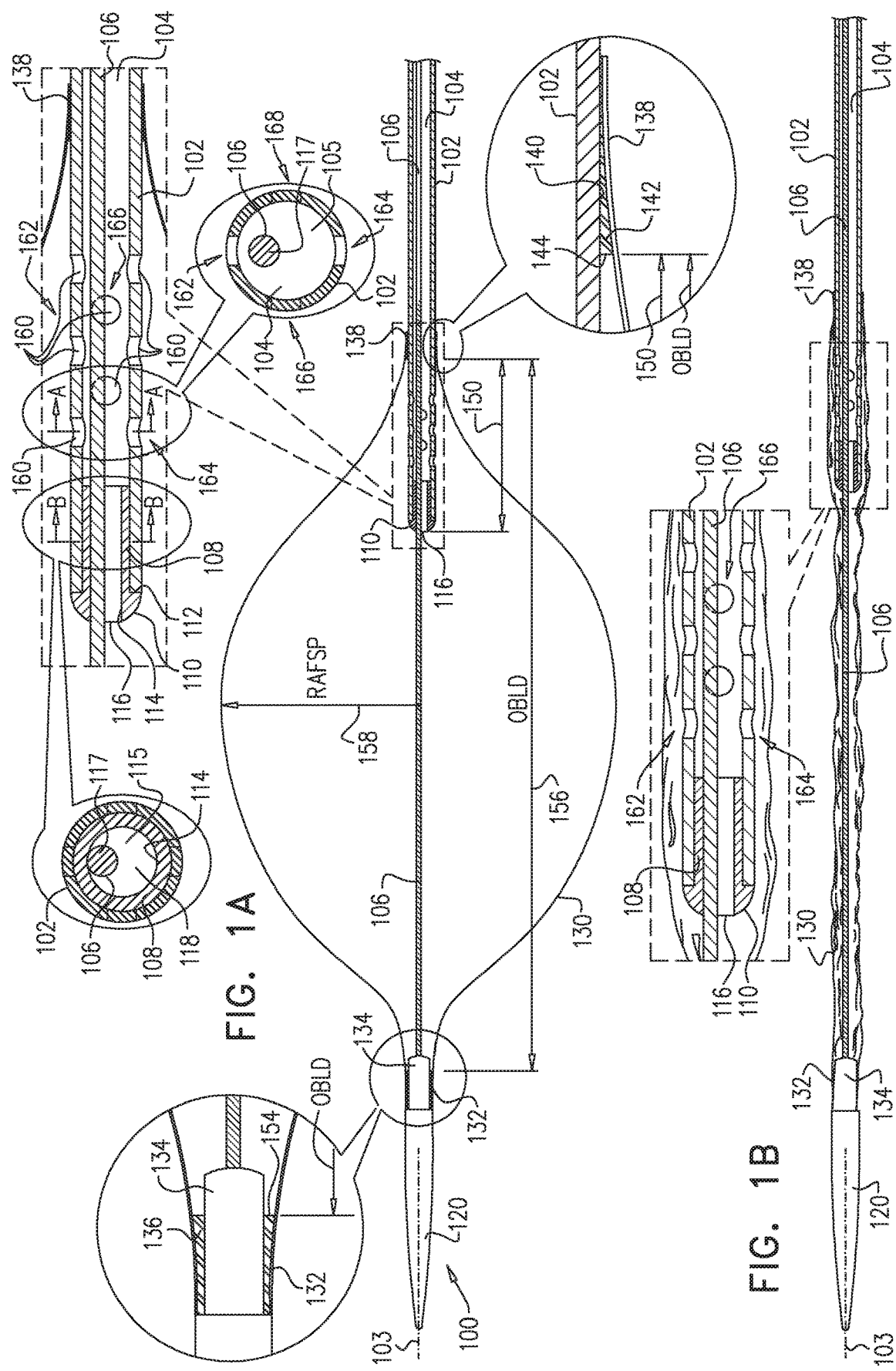

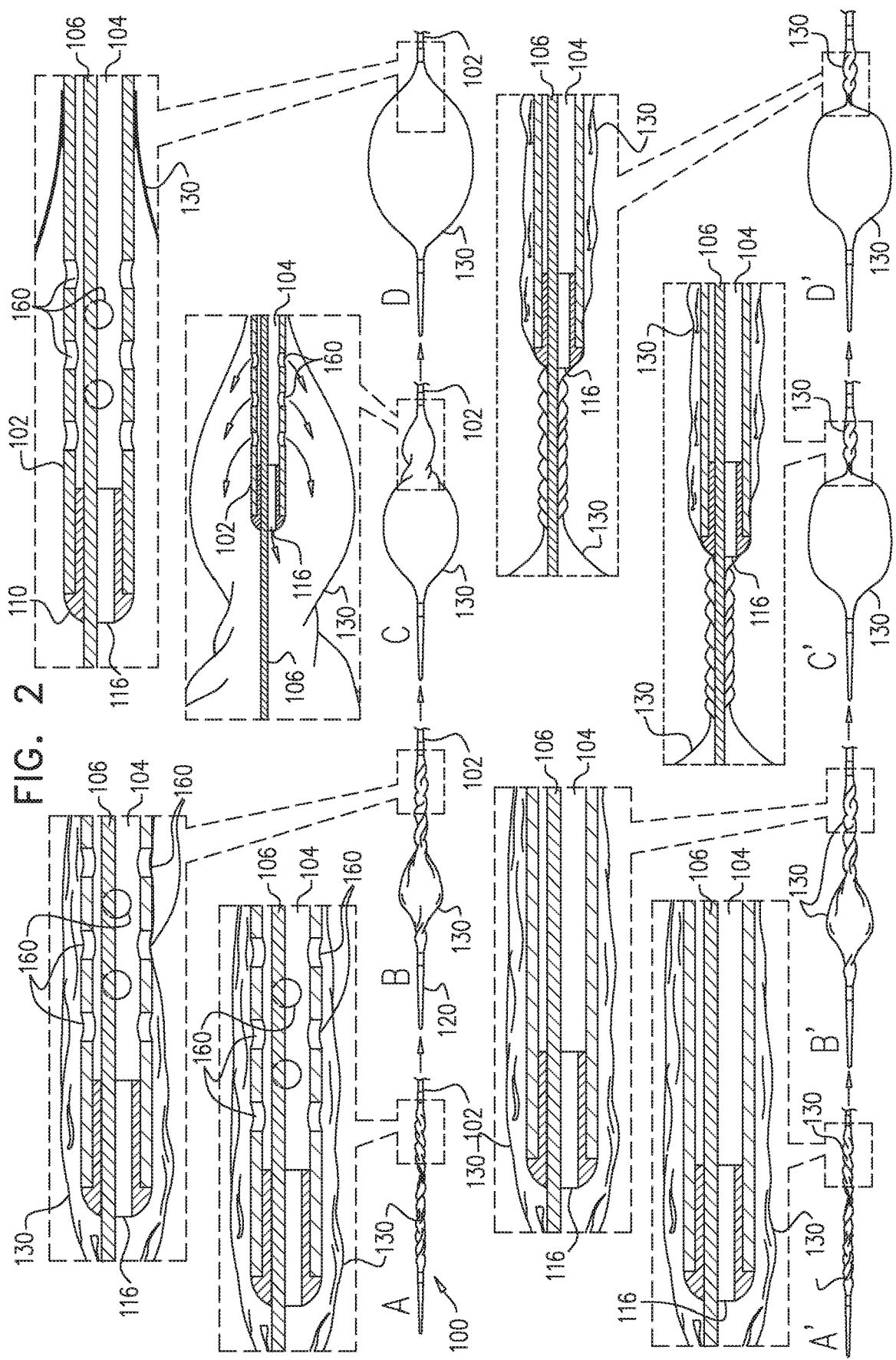

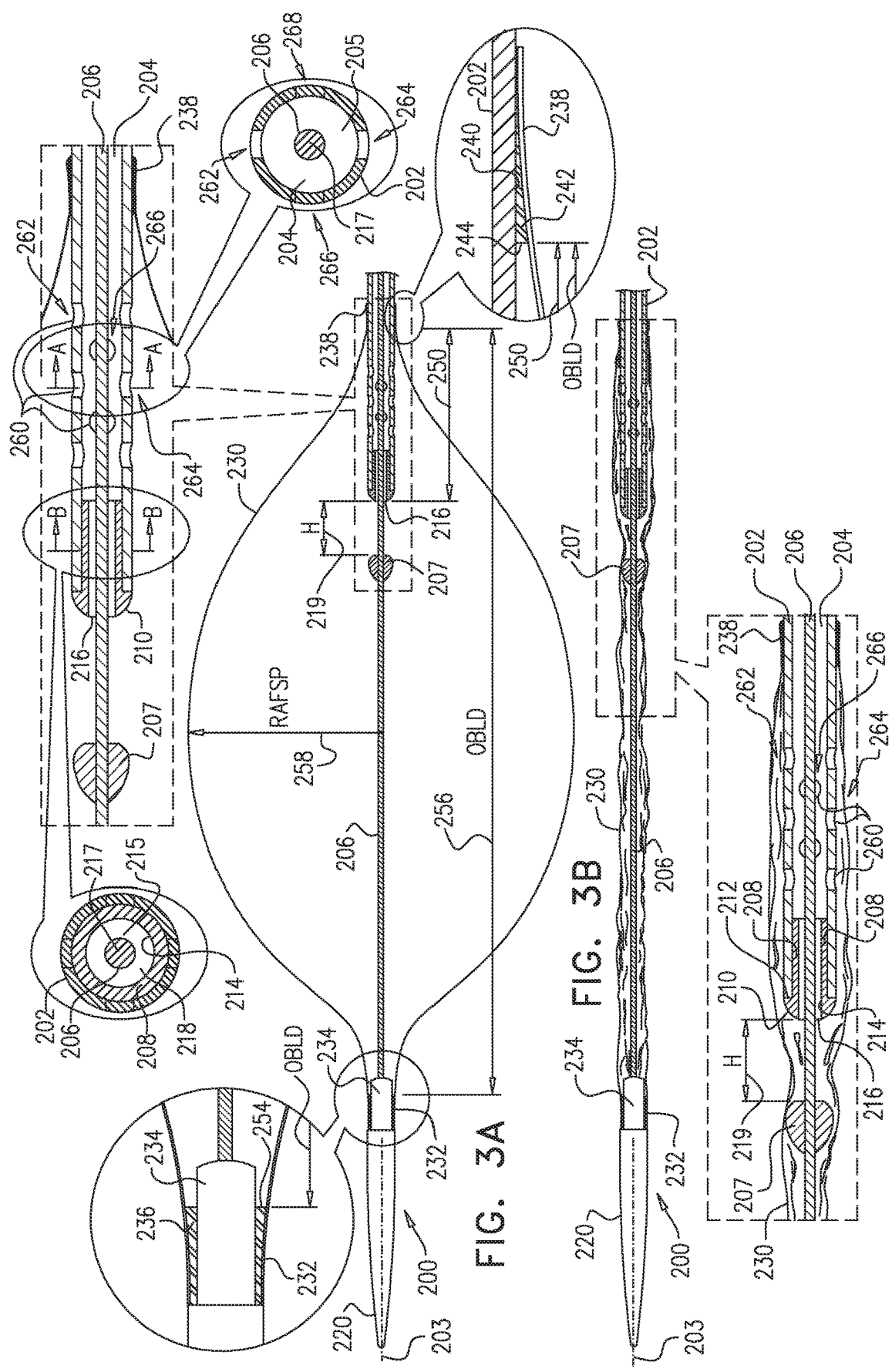

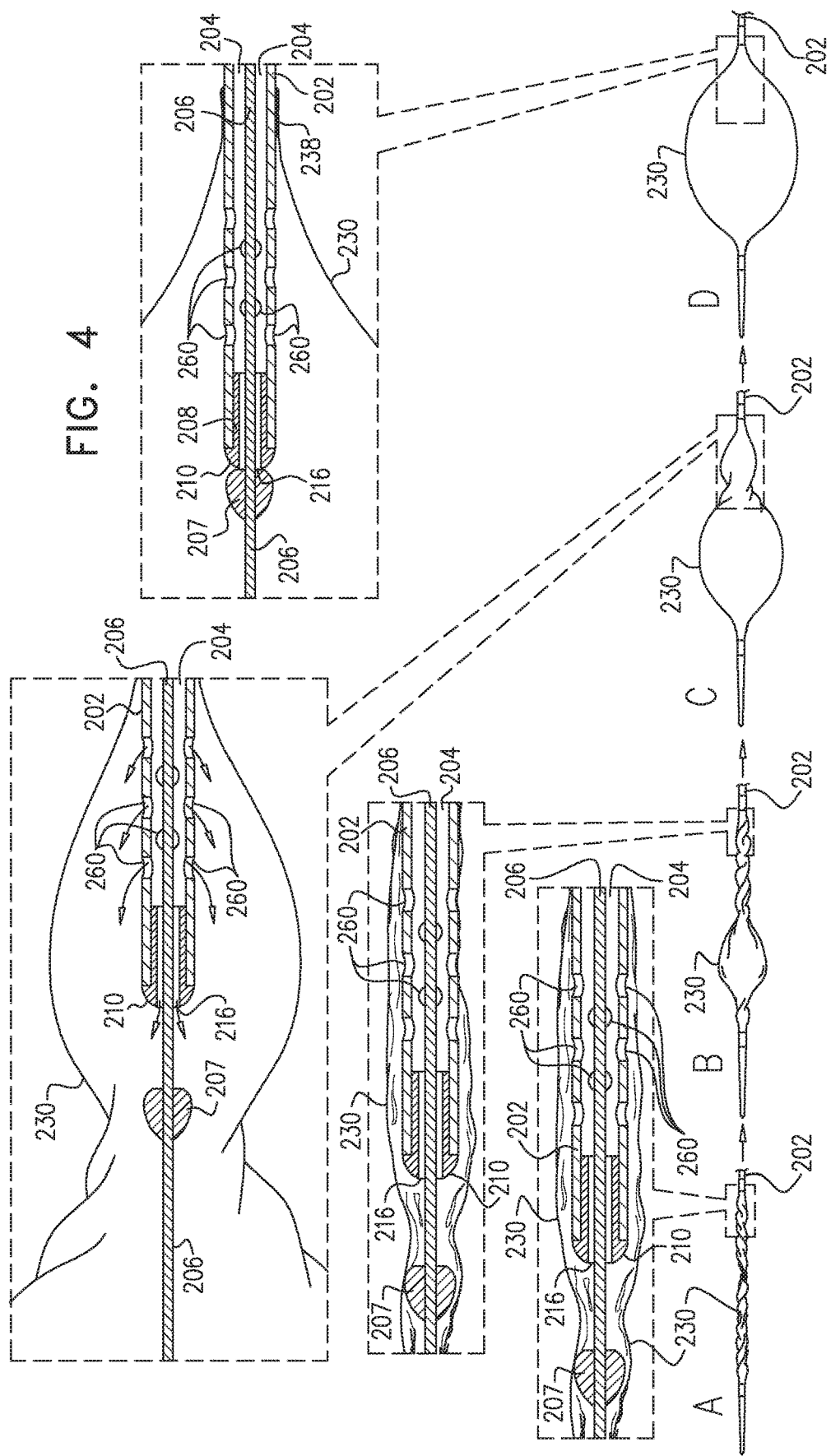

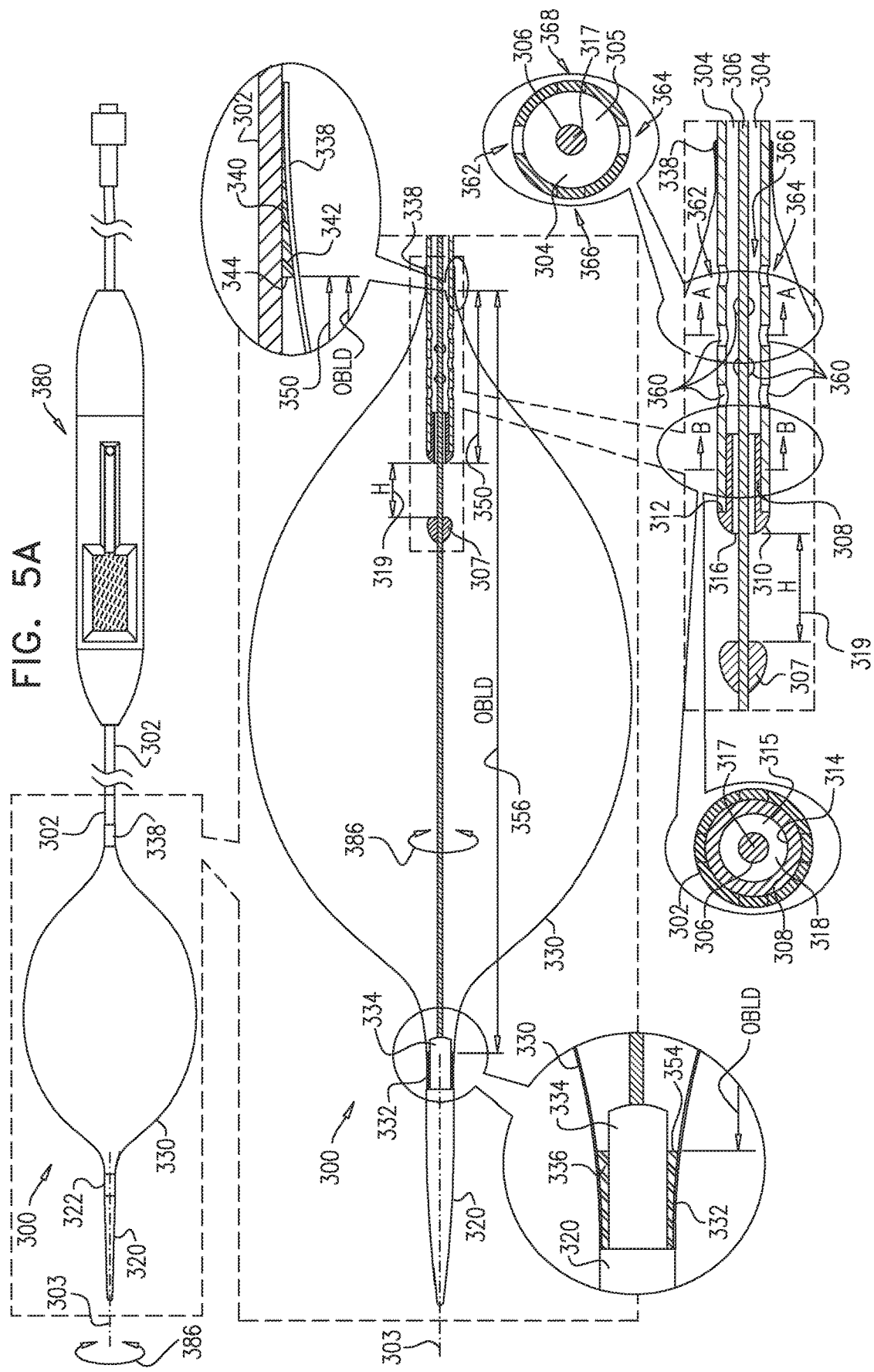

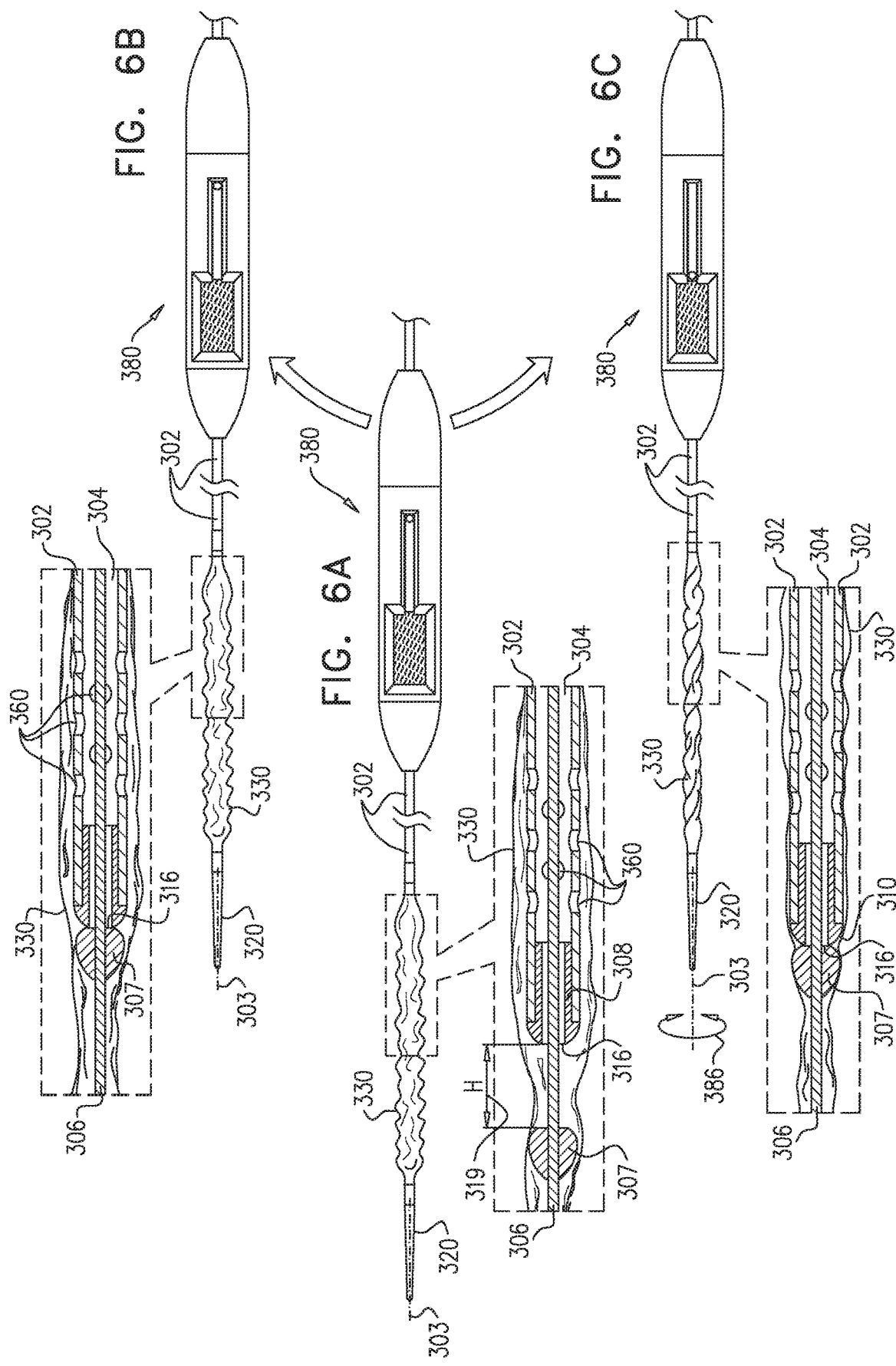

FIG. 10A
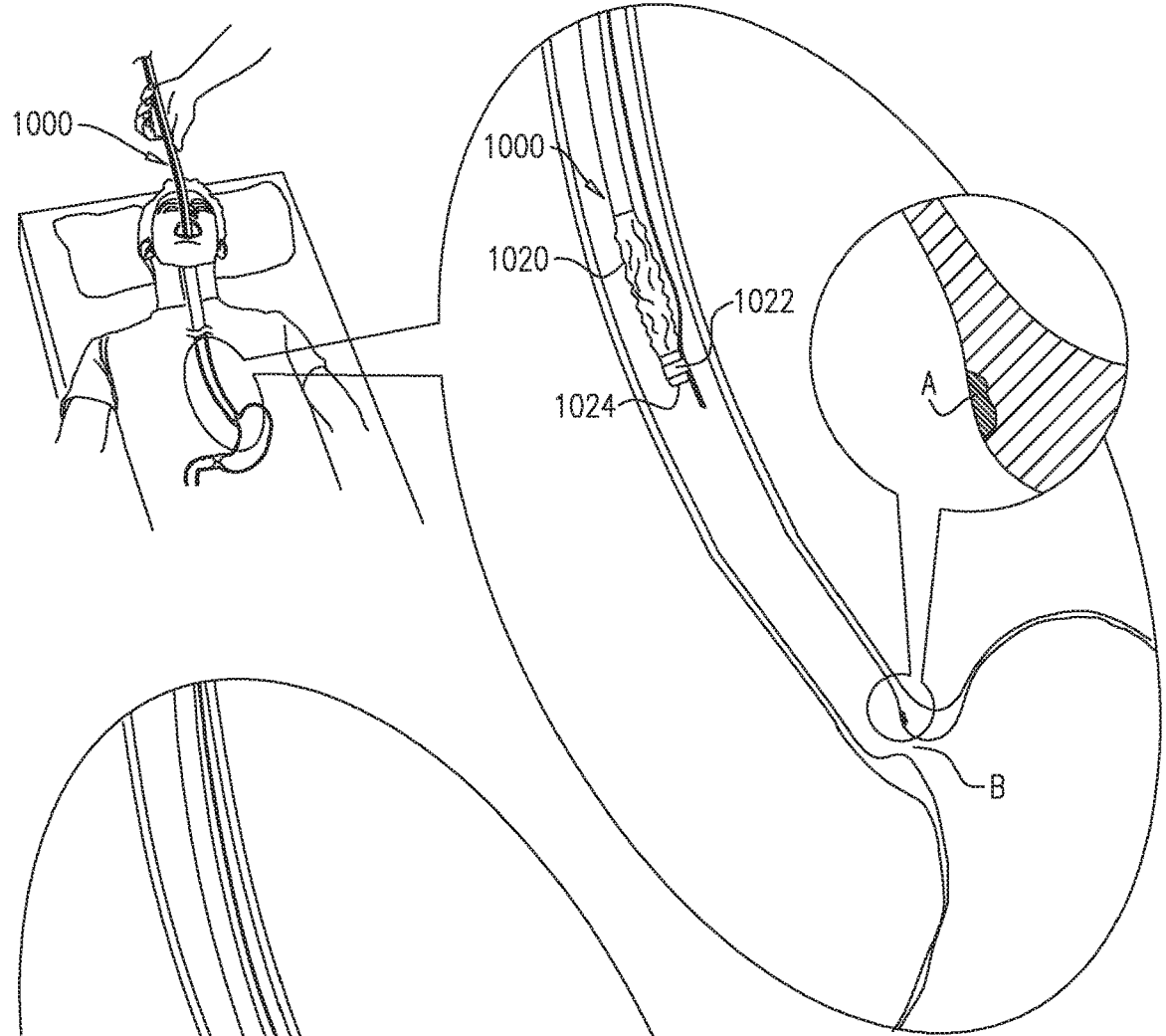
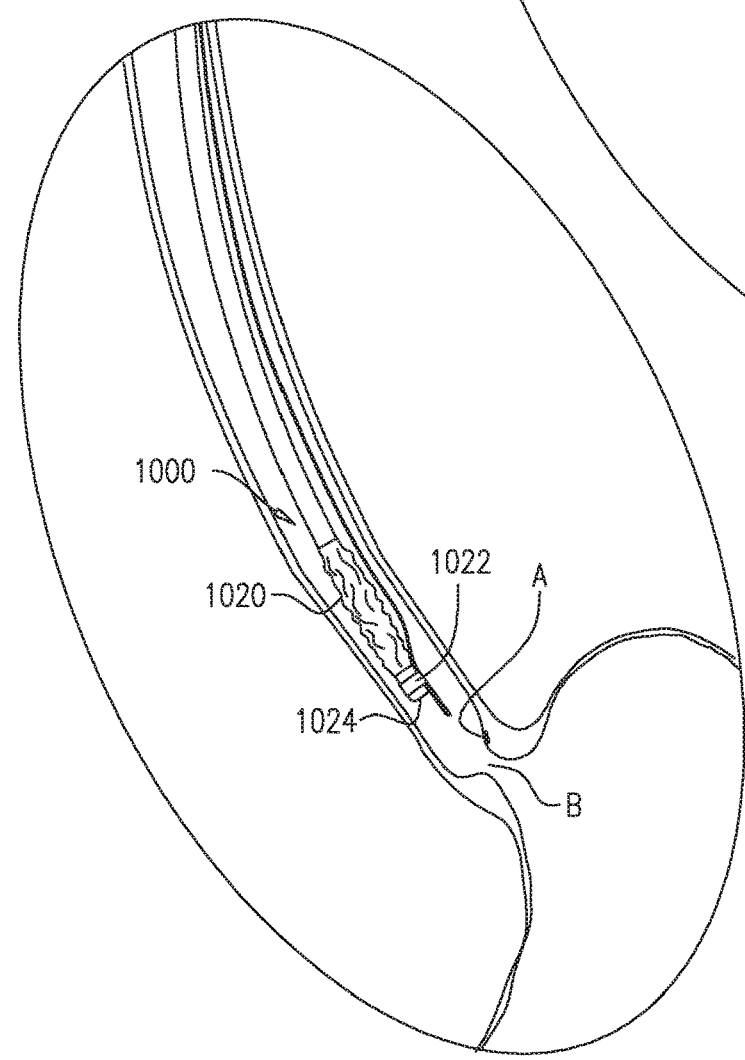
FIG. 10B

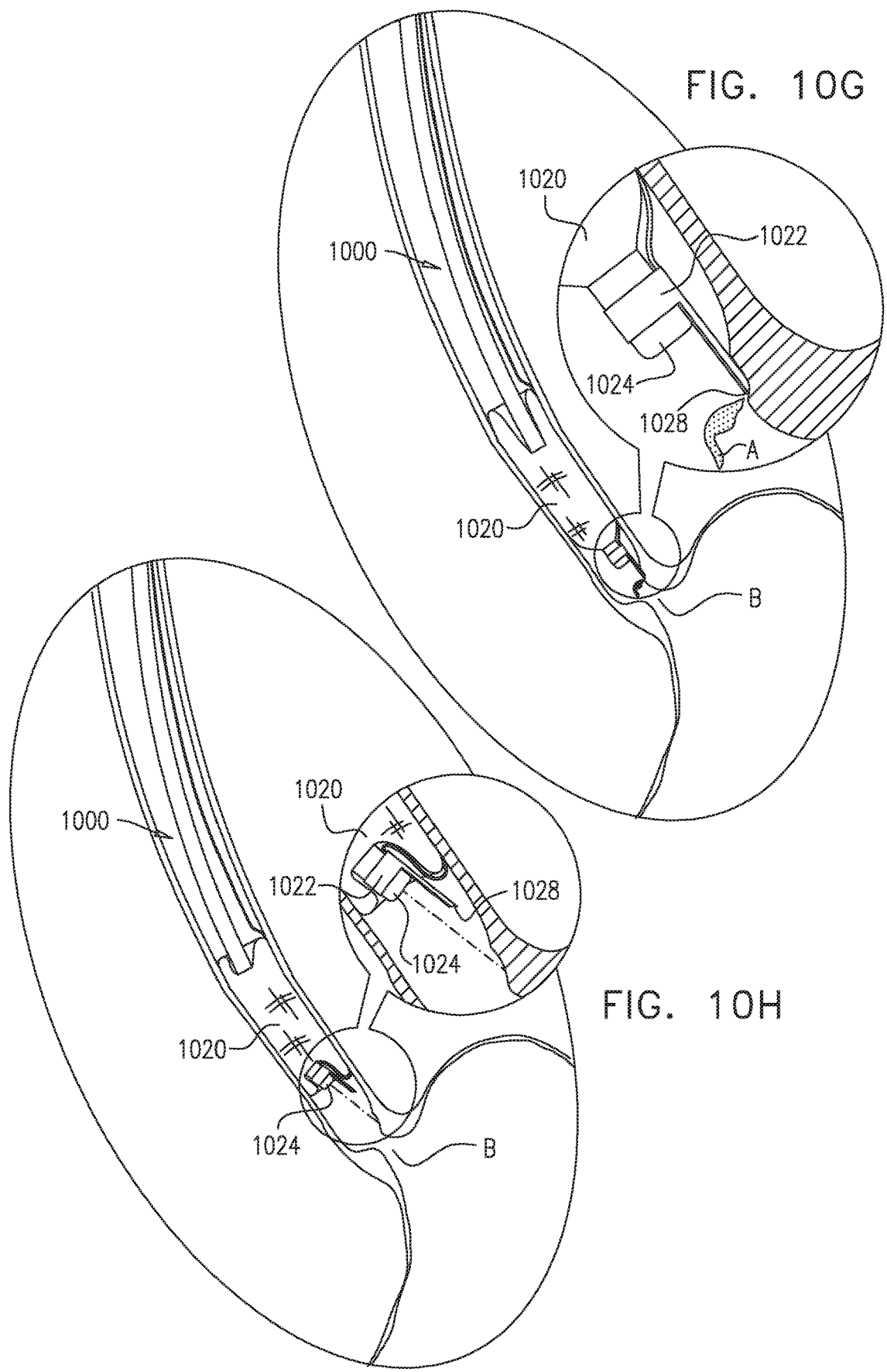

ENDOSCOPY DEVICES AND APPLICATIONS THEREOF

CROSS-REFERENCE TO RELATED APPLICATIONS

This application is a U.S. National Phase Application under 35 U.S.C. 371 of International Application No. PCT/IL2013/050894, which has an international filing date of Oct. 31, 2013, and which claims the benefit of U.S. Provisional Patent Application Ser. No. 61/796,099 filed on Nov. 2, 2012, entitled "MANTPULABLE BALLOON CATHETER" and U.S. Provisional Patent Application Ser. No. 61/796,100 filed on Nov. 2, 2012 entitled "BALLOON ENDOSCOPE WITH LONGITUDINAL DISPLACEMENT", the disclosures of which are hereby incorporated by reference.

The following patents and patent applications are believed to be related to the claimed subject matter of the present application:

Applicant's Published PCT Patent Applications WO2010/137025 and WO2011/111040.

Reference is also made to applicant's Published PCT Patent Applications WO2005/074377; WO2007/017854; WO2007/135665; WO2008/004228; WO2008/142685; WO2009/122395; WO2010/046891; WO2010/137025; WO2011/111040, and WO/2012/120492 the disclosures of which are hereby incorporated by reference.

FIELD OF THE INVENTION

The present invention relates to balloon endoscopes and catheters generally.

BACKGROUND OF THE INVENTION

Various types of balloon endoscopes and catheters are known in the art.

SUMMARY OF THE INVENTION

The present invention seeks to provide improved balloon endoscopes and catheters.

There is thus provided in accordance with a preferred embodiment of the present invention a balloon catheter assembly including an elongate catheter tube including a lumen having a first cross sectional area, a wire extending through the lumen, and an inflatable balloon mountably associated, at a rearward end thereof, with the elongate catheter tube and mountably associated, at a forward end thereof, with the wire, the elongate catheter tube being formed with a plurality of balloon inflation apertures communicating with the lumen, the plurality of balloon inflation apertures having a total aperture cross sectional area which exceeds the first cross sectional area of the lumen and including at least two apertures being arranged at different azimuthal locations along the catheter tube underlying the balloon and the balloon being characterized by an inflated state having a ratio of maximum inflated diameter to length of more than 0.4 and a corresponding deflated state wherein at least a first portion of the balloon is capable of being twisted relative to at least a second portion of the balloon, resulting in at least partial blockage of at least one but not all of the plurality of balloon inflation apertures.

Preferably, the at least two apertures being arranged at different azimuthal locations along the catheter tube underlying the balloon, are azimuthally offset by approximately 90 degrees. Yet preferably, the at least two apertures being arranged at different azimuthal locations along the catheter tube underlying the balloon, are azimuthally offset by approximately 180 degrees.

Preferably, the wire is fixedly associated with a forward edge of the tube. In accordance with a preferred embodiment of the present invention the wire is retractable into the tube to a maximal predetermined extent.

Preferably, the total aperture cross sectional area of the plurality of balloon inflation apertures is greater than 1.2 times the first cross sectional area of the lumen. More preferably, the total aperture cross sectional area of the plurality of balloon inflation apertures is greater than 1.5 times the first cross sectional area of the lumen.

In accordance with a preferred embodiment of the present invention the balloon catheter assembly also includes an end element having an apertured front face surface, mounted interiorly and forwardly of a forward edge of the catheter tube. Additionally, the end element is located entirely forwardly of the at least two apertures. Additionally or alternatively, the wire is fixedly attached to the end element.

Preferably, the balloon catheter assembly also includes a forward-facing aperture defined in a front face of the tube and having a forward inflation cross-sectional area, the forward facing aperture being in fluid communication with the lumen of the tube. Additionally, the forward inflation cross-sectional area is between 25%-90% of the first cross sectional area.

There is also provided in accordance with another preferred embodiment of the present invention a balloon catheter assembly including an elongate catheter tube including a lumen having a first cross sectional area and a forward-facing aperture defined in a front face of the tube, being in fluid communication with the lumen and having a forward inflation cross-sectional area, a wire extending through the lumen and an inflatable balloon mountably associated, at a rearward end thereof, with the elongate catheter tube and mountably associated, at a forward end thereof, with the wire, the elongate catheter tube being formed with a plurality of balloon inflation side apertures formed in the tube underlying the balloon and communicating with the lumen, the plurality of balloon inflation side apertures having a total aperture cross sectional area which exceeds the forward inflation cross-sectional area and including at least two side apertures being arranged at different azimuthal locations along the catheter tube underlying the balloon and the balloon being characterized by an inflated state having a ratio of maximum inflated diameter to length of more than 0.4 and a corresponding deflated state wherein at least a first portion of the balloon is capable of being twisted relative to at least a second portion of the balloon, resulting in at least partial blockage of at least one but not all of the plurality of balloon inflation side apertures.

Preferably, the wire is fixedly associated with a forward edge of the tube. In accordance with a preferred embodiment of the present invention the wire is retractable into the tube to a maximal predetermined extent.

Preferably, the total aperture cross sectional area of the plurality of balloon inflation side apertures is greater than 1.3 times the forward inflation cross-sectional area. More preferably, the total aperture cross sectional area of the plurality of balloon inflation side apertures is greater than 1.7 times the forward inflation cross-sectional area.

In accordance with a preferred embodiment of the present invention the balloon catheter assembly also includes an end element having an apertured front face surface, mounted interiorly and forwardly of a forward edge of the catheter tube. Additionally, the end element is located entirely forwardly of the at least two side apertures. Additionally or alternatively, the wire is fixedly attached to the end element.

Preferably, the forward inflation cross-sectional area is between 25%-90% of the first cross sectional area.

There is further provided in accordance with yet another preferred embodiment of the present invention a balloon catheter assembly including an elongate catheter tube including a lumen having a first cross sectional area; a wire extending through the lumen and being rotatable relative to the elongate catheter tube and axially displaceable relative to the elongate catheter tube, an inflatable balloon mountably associated, at a rearward end thereof, with the elongate catheter tube and mountably associated, at a forward end thereof, with the wire, the inflatable balloon being furlable by rotation of the wire relative to the elongate catheter tube and the wire being rearwardly axially displaceable by no greater than a first distance relative to the elongate catheter tube as a result of the balloon being furled and a limiting element fixedly associated with the wire at a location underlying the inflatable balloon, the location being forward of a forward end of the elongate catheter tube by a second distance when the wire is in a fully forwardly extended state relative to the tube, the second distance being a function of the first distance.

In accordance with a preferred embodiment of the present invention the second distance is longer than the first distance. Alternatively, the first distance is longer than the second distance.

Preferably, a ratio of the second distance to the first distance is greater than 1.3. More preferably, a ratio of the second distance to the first distance is greater than 1.5. Most preferably, a ratio of the second distance to the first distance is greater than 2.

In accordance with an alternative preferred embodiment of the present invention a ratio of the first distance to the second distance is greater than 1.3. More preferably, a ratio of the first distance to the second distance is greater than 1.5. Most preferably, a ratio of the first distance to the second distance is greater than 2.

Preferably, the second distance is in the range of 5-20 millimeters. More preferably, the second distance is in the range of 6-12 millimeters.

There is even further provided in accordance with still another preferred embodiment of the present invention a balloon catheter assembly including an elongate catheter tube having an elongate axis including a lumen having a first cross sectional area, a wire extending through the lumen and an inflatable balloon mountably associated, at a rearward end thereof, with the elongate catheter tube and mountably associated, at a forward end thereof, with the wire, the balloon being characterized by an inflated state having a ratio of maximum inflated diameter to length of more than 0.4 and the elongate catheter tube being formed with a plurality of balloon inflation apertures communicating with the lumen, the plurality of balloon inflation apertures having a total aperture cross sectional area which exceeds the first cross sectional area of the lumen and including at least two apertures being arranged at different azimuthal locations along the catheter tube underlying the balloon, the plurality of balloon inflation apertures being configured to prevent total blockage of all of the plurality of balloon inflation apertures when at least a first portion of the balloon is twisted about the elongate axis relative to at least a second portion of the balloon by at least 720 degrees.

Preferably, the wire is fixedly associated with a forward edge of the tube. In accordance with a preferred embodiment of the present invention the wire is retractable into the tube to a maximal predetermined extent.

Preferably, the total aperture cross sectional area of the plurality of balloon inflation apertures is greater than 1.2 times the first cross sectional area of the lumen. More preferably, the total aperture cross sectional area of the plurality of balloon inflation apertures is greater than 1.5 times the first cross sectional area of the lumen.

In accordance with a preferred embodiment of the present invention the balloon catheter assembly also includes an end element having an apertured front face surface, mounted interiorly and forwardly of a forward edge of the catheter tube. Additionally, the wire is fixedly attached to the end element.

Preferably, the balloon catheter assembly also includes a forward-facing aperture defined in a front face of the tube and having a forward inflation cross-sectional area, the forward facing aperture being in fluid communication with the lumen of the tube. Additionally, the forward inflation cross-sectional area is between 25%-90% of the first cross sectional area.

There is still further provided in accordance with yet another preferred embodiment of the present invention a balloon catheter assembly including an elongate catheter tube having an elongate axis including a lumen having a first cross sectional area and a forward-facing aperture defined in a front face of the tube, being in fluid communication with the lumen and having a forward inflation cross-sectional area, a wire extending through the lumen and an inflatable balloon mountably associated, at a rearward end thereof, with the elongate catheter tube and mountably associated, at a forward end thereof, with the wire, the balloon being characterized by an inflated state having a ratio of maximum inflated diameter to length of more than 0.4 and the elongate catheter tube being formed with a plurality of balloon inflation side apertures communicating with the lumen, the plurality of balloon inflation side apertures having a total aperture cross sectional area which exceeds the forward inflation cross-sectional area and including at least two side apertures being arranged at different azimuthal locations along the catheter tube underlying the balloon, the plurality of balloon inflation side apertures being configured to provide inflation of the balloon therethrough when at least a first portion of the balloon is twisted about the elongate axis relative to at least a second portion of the balloon by at least 720 degrees, thereby at least partially sealing the forward-facing aperture.

Preferably, the wire is fixedly associated with a forward edge of the tube. In accordance with a preferred embodiment of the present invention the wire is retractable into the tube to a maximal predetermined extent.

Preferably, the total aperture cross sectional area of the plurality of balloon inflation side apertures is greater than 1.3 times the forward inflation cross-sectional area. More preferably, the total aperture cross sectional area of the plurality of balloon inflation side apertures is greater than 1.7 times the forward inflation cross-sectional area.

In accordance with a preferred embodiment of the present invention the balloon catheter assembly also includes an end element having an apertured front face surface, mounted interiorly and forwardly of a forward edge of the catheter tube. Additionally, the end element is located entirely forwardly of the at least two side apertures. Additionally or alternatively, the wire is fixedly attached to the end element.

There is yet further provided in accordance with another preferred embodiment of the present invention an anchoring balloon endoscope including an elongate endoscope having a forward end portion, a substantially non-stretchable, inflatable anchoring balloon mounted on the elongate endoscope, the substantially non-stretchable, inflatable anchoring balloon having first and second sealing attachment locations on the elongate endoscope, which are separated by a distance A along the elongate endoscope, the substantially non-stretchable, inflatable anchoring balloon having a balloon surface axial cross-sectional extent B extending between the first and second sealing attachment locations, which extent is at least 1.5 times greater than the distance A, the substantially non-stretchable, inflatable balloon, when inflated within a cylindrical element having an inner radius D that is coaxial with and surrounding at least a portion of the elongate endoscope, having an anchoring surface in contact with an inner surface of the cylindrical element whose axial cross-sectional extent is C, where: A<C<B and C−A>m×D, where m>1.

In accordance with a preferred embodiment of the present invention the balloon endoscope is configured to allow, when inflated within the cylindrical element, simultaneous radial anchoring of the endoscope and axial forward and backward movement of the forward end portion of the endoscope.

Preferably, m is greater than 1.5. More preferably, m is greater than 2.

In accordance with a preferred embodiment of the present invention the extent B is greater than twice the distance A.

In accordance with a preferred embodiment of the present invention the endoscope may be pushed forwardly axially while anchored in the cylindrical element with a maximum forward displacement E, where:

$$E > n \times D, \text{ where } n \geq 1.$$

Preferably, n is greater than 1.5. More preferably, n is greater than 2.

In accordance with a preferred embodiment of the present invention the endoscope may be pushed rearwardly axially while anchored in the cylindrical element with a maximum rearward displacement F, where: F>k×D, where k≥1.

Preferably, k is greater than 1.5. More preferably, k is greater than 2.

In accordance with a preferred embodiment of the present invention the balloon inflates to a generally double trapezoidal axial cross sectional free shape at a pressure of 5-10 mbar. Alternatively, the balloon inflates to a generally double rectangular axial cross sectional free shape at a pressure of 5-10 mbar.

In another alternative embodiment of the present invention the balloon inflates to a generally double elliptical axial cross sectional free shape at a pressure of 5-10 mbar. Additionally, the generally double elliptical axial cross sectional free shape of the balloon has a maximal longitudinal extent L and a maximal radial extent R, the maximal longitudinal extent L being greater than the distance A. Additionally, the maximal radial extent R is greater than the distance A. Preferably, a ratio between radial extent R and distance A is in the range of 0.8-1.6.

There is still further provided in accordance with yet another preferred embodiment of the present invention an endoscopy method including providing an anchoring balloon endoscope including an elongate endoscope having a forward tip and an inflatable anchoring balloon mounted on the elongate endoscope rearwardly and adjacent the forward tip, inserting the anchoring balloon endoscope into a generally tubular body portion with the balloon in a deflated state, inflating the balloon to anchoring engagement with the generally tubular body portion and radially anchoring the balloon endoscope thereto, and axially displacing the forward tip of the elongate endoscope along a longitudinal axis of the elongate endoscope while the balloon endoscope is anchored and radially stabilized in the generally tubular body portion.

Preferably, the step of axially displacing the forward tip of the elongate endoscope includes the step of forwardly displacing the forward tip of the elongate endoscope. Yet preferably, the step of axially displacing the forward tip of the elongate endoscope includes the step of rearwardly displacing the forward tip of the elongate endoscope.

In an alternative embodiment of the present invention forwardly displacing the forward tip of the elongate endoscope includes displacing the forward tip forwardly by a distance which is greater than the radius of the generally tubular body portion. In another alternative embodiment of the present invention rearwardly displacing the forward tip of the elongate endoscope includes displacing the forward tip rearwardly by a distance which is greater than the radius of the generally tubular body portion.

Preferably, the endoscopy method also includes mounting a therapeutic device on the forward tip of the endoscope, and axially displacing the forward tip of the endoscope while the balloon endoscope is radially anchored, thereby bringing the therapeutic device into operative engagement with a pathology in the generally tubular body portion.

According to a particular embodiment of the present invention, the therapeutic device is an ablation device, the pathology is a Barrett pathology, and bringing the therapeutic device into operative engagement with a pathology includes bringing the ablation device into contact with a Barrett pathology.

Additionally or alternatively, the endoscopy method also includes at least one of the steps of:
performing sideways deflection of the forward tip of the endoscope for allowing a forward-looking optics mounted on the forward tip to detect a pathology;
performing ablation of a pathological tissue;
inspecting the generally tubular body portion by the optics while the endoscope is radially anchored in said generally tubular body portion;
deflating the balloon; and
withdrawing the balloon endoscope from the generally tubular body portion.

BRIEF DESCRIPTION OF THE DRAWINGS

The present invention will be understood and appreciated more fully from the following description, taken in conjunction with the drawings in which:

FIGS. 1A & 1B are simplified illustrations of a balloon catheter constructed and operative in accordance with a preferred embodiment of the present invention in respective inflated and deflated states;

FIG. 2 is a simplified illustration of stages of inflation of the balloon catheter of FIGS. 1A-1B as compared with corresponding steps of inflation of a conventional balloon catheter;

FIGS. 3A & 3B are simplified illustrations of a balloon catheter constructed and operative in accordance with another preferred embodiment of the present invention in respective inflated and deflated states;

FIG. 4 is a simplified illustration of steps of inflation of the balloon catheter of FIGS. 3A-3B;

FIGS. 5A & 5B are simplified illustrations of a balloon catheter constructed and operative in accordance with yet another preferred embodiment of the present invention in respective inflated and deflated states;

FIG. 6A is a simplified illustration of the balloon catheter of FIGS. 5A & 5B in a deflated unfurled fully extended state;

FIG. 6B is a simplified illustration of the balloon catheter of FIGS. 5A & 5B in a deflated unfurled fully retracted state;

FIG. 6C is a simplified illustration of the balloon catheter of FIGS. 5A & 5B in a deflated furled state;

FIGS. 10A, 10B, 10C, 10D, 10E, 10F, 10G, 10H, 10I and 10J are simplified illustrations of one clinical application of the balloon endoscope of any of FIGS. 7A-9D.

DETAILED DESCRIPTION OF PREFERRED EMBODIMENTS

Figure 5B:
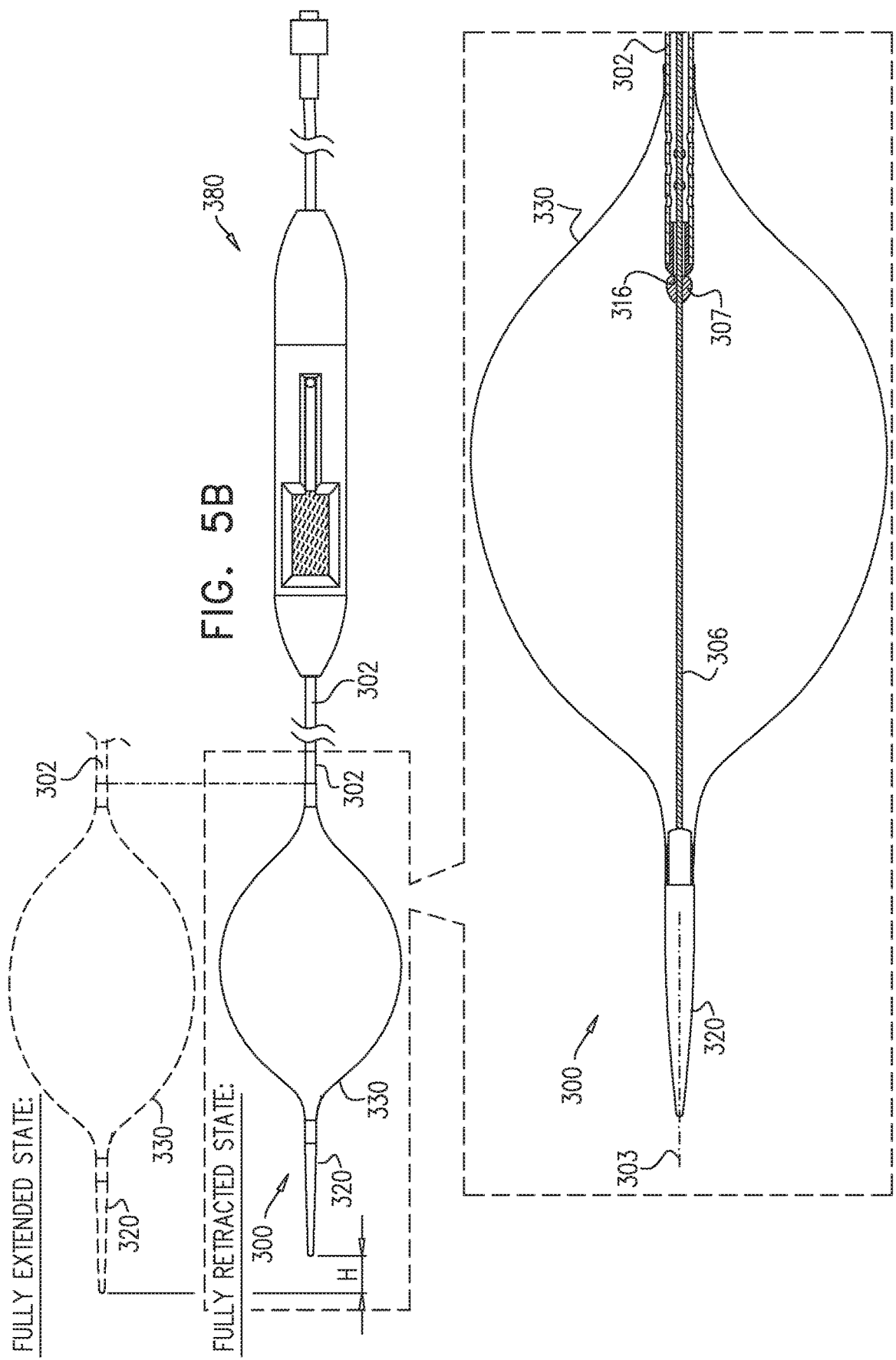

Reference is now made to FIGS. 1A & 1B, which are simplified illustrations of a balloon catheter constructed and operative in accordance with a preferred embodiment of the present invention in respective inflated and deflated states.

As seen in FIGS. 1A & 1B, there is a balloon catheter assembly 100 including an elongate catheter tube 102, here shown extending axially along a longitudinal axis 103 and including a lumen 104 having a lumen cross sectional area 105, here also termed a first cross-sectional area. A wire 106, typically formed of stainless steel or nitinol, extends through the catheter tube 102. An end element 108, preferably having a smoothly rounded apertured front face surface 110, is mounted interiorly and forwardly of a forward edge 112 of catheter tube 102 and defines an inner, generally circular cylindrical surface 114 having an end element cross-sectional area 115, here also termed a second cross-sectional area.

Preferably wire 106 extends through a forward-facing aperture 116 defined by apertured front face 110 and is fixedly attached to inner surface 114 of end element 108, such as by adhesive, welding or soldering, as applicable. The cross-sectional area of wire 106, here designated by reference numeral 117, is preferably substantially less than the end element cross-sectional area 115. The end element cross-sectional area 115 at aperture 116 minus the cross-sectional area 117 of wire 106 defines a forward inflation cross-sectional area 118, here also termed a third cross-sectional area.

Typical radial dimensions of the first and second cross-sectional areas referenced above are as follows:

First cross-sectional area 105—Diameter preferably between 1-2 mm, more preferably between 1.2-1.8 mm and most preferably between 1.4-1.8 mm.

Second cross-sectional area 115—Diameter preferably between 0.5-1.8 mm, more preferably between 0.8-1.7 mm and most preferably between 1.2-1.6 mm.

Diameter of wire 106 is preferably between 0.3-1 mm, more preferably between 0.35-0.8 mm, and most preferably between 0.4-0.7 mm.

Typical area dimensions of the first, second and third cross-sectional areas referenced above are as follows:

First cross-sectional area 105—Preferably between 0.75-3 mm$^2$, more preferably between 1.1-2.5 mm$^2$, and most preferably between 1.5-2.5 mm$^2$, Second cross-sectional area 115—Preferably between 0.2-2.5 mm$^2$, more preferably between 0.5-2.2 mm$^2$, and most preferably between 1.1-2 mm$^2$, Third cross-sectional area 118—Preferably between 0.1-2.4 mm$^2$, more preferably between 0.3-2 mm$^2$, and most preferably between 0.5-1.8 mm$^2$, Typical ratios between the first, second and third cross-sectional areas are as follows:

The second cross-sectional area 115 is preferably between 30-95% of the first cross-sectional area 105, more preferably between 50-90% of the first cross-sectional area 105 and most preferably between 65-85% of the first cross-sectional area 105.

The third cross-sectional area 118 is preferably between 25-90% of the first cross-sectional area 105, more preferably between 40-85% of the first cross-sectional area 105 and most preferably between 60-80% of the first cross-sectional area 105.

Preferably a forward catheter tip 120 is fixed to a forward end of wire 106. A generally non-stretchable inflatable balloon 130 is preferably sealingly fixed at a forward neck portion 132 thereof to a corresponding cylindrical portion 134 of tip 120, as by an adhesive layer 136. Inflatable balloon 130 is preferably sealingly fixed at a rearward neck portion 138 thereof to an outer surface portion 140 of catheter tube 102, as by an adhesive layer 142.

A forward-facing edge 144 of adhesive layer 142 preferably lies at a rearward balloon mounting distance 150 rearwardly of aperture 116, preferably between 5-50 mm. A rearward-facing edge 154 of adhesive layer 136 is separated from the forward-facing edge 144 of adhesive layer 140 by an overall balloon length distance OBLD, here designated by reference numeral 156, which is preferably between 50-140 mm.

Preferably balloon 130, when inflated to a free-shape pressure, typically 5-10 mbar, has a maximum radius RAFSP, here designated by reference 158, which is preferably between 30-70 mm, and more preferably between 35-65 mm. Preferably the ratio between RAFSP and OBLD (namely RAFSP/OBLD) is higher than 0.4, and more preferably this ratio is between 0.5-1.

It is a particular feature of the present invention that the catheter tube 102 is formed with a plurality of balloon inflation side apertures 160 communicating with lumen 104, the plurality of balloon inflation apertures including at least two apertures being arranged at different azimuthal locations along the catheter tube 102 underlying balloon 130. All of apertures 160 together have a combined total aperture cross sectional area which preferably exceeds the third cross sectional area 118 and more preferably exceeds the first cross-sectional area 105.

The total aperture cross sectional area of side apertures 160 is preferably greater than 1.3 times the forward inflation cross-sectional area 118, more preferably greater than 1.7 times the forward inflation cross-sectional area 118, and most preferably greater than 2 times the forward inflation cross-sectional area 118. In accordance with a preferred configuration of side apertures 160, the total aperture cross sectional area of side apertures 160 is not more than 4 times the lumen cross sectional area 105.

The total aperture cross sectional area of side apertures 160 is preferably greater than 1.2 times the lumen cross sectional area 105, more preferably greater than 1.5 times the lumen cross sectional area 105, and most preferably greater than 2 times the lumen cross sectional area 105. In accordance with a yet preferred configuration of side apertures 160, the total aperture cross sectional area of side apertures 160 is not more than 5 times the lumen cross sectional area 105.

It is appreciated that providing a large total aperture cross sectional area of side apertures 160 allows reduced resistance to fluid passage through side apertures 160 and faster inflation and deflation of balloon 130 through lumen 104 of tube 102. It is also appreciated that limiting the total aperture cross sectional area of side apertures 160 to be not greater than 4 times the lumen cross sectional area 105, may be beneficial for maintaining the mechanical strength of the front portion of tube 102 underlying balloon 130.

In the illustrated embodiment, a total of ten balloon inflation side apertures 160 are provided. A preferred arrangement, illustrated in FIGS. 1A & 1B includes two mutually oppositely directed rows 162 and 164 of three apertures 160 each and two mutually oppositely directed rows 166 and 168 of two apertures 160 each, wherein each of rows 162 and 164 is azimuthally offset relative to axis 103 from an adjacent one of rows 166 and 168 by approximately 90 degrees and further wherein each of the apertures 160 in rows 166 and 168 is located axially along axis 103 intermediate and generally equidistant between each pair of adjacent apertures 160 in rows 162 and 164.

It is a further particular feature of the present invention that the balloon is characterized by having an inflated state and a corresponding deflated state wherein at least a first portion of the balloon is capable of being twisted relative to at least a second portion of the balloon, resulting in at least partial blockage of at least one but not all of the plurality of the balloon side apertures 160.

Reference is now made to FIG. 2, which is a simplified illustration of stages A, B, C & D of inflation of the balloon catheter of FIGS. 1A & 1B as compared with corresponding steps of inflation A', B', C' and D' of a conventional balloon catheter. Stages A and A' are identical and show the balloon catheter of FIG. 1A and a conventional catheter, respectively, in a fully deflated center-twisted state.

Stage B is an initial inflation state, wherein pressurized air enters the interior of balloon 130 through apertures 116 and 160. Stage B' is similar to Stage B.

Stage C is a further inflation state, wherein pressurized air continues to enter the interior of balloon 130 through apertures 116 and 160. In Stage C' however pressurized air can only enter the interior of balloon 130 through aperture 116 and aperture 116 is seen to be at least partially blocked, thereby preventing full inflation of balloon 130.

It is appreciated that partial or complete blockage of forward-facing aperture 116 may occur, for example, during inflation of balloon 130 inside a body cavity such as the intestine during endoscopic procedure, or during inflation within a generally cylindrical tube. During such inflation, the frictional contact of the balloon surface with the inner wall of the body cavity or the cylindrical tube maintains the twisting of balloon 130 and prevents it from untwisting freely when the balloon is being inflated. Thus, when air fills the balloon through forward-facing aperture 116 during inflation and the center portion of the balloon expands radially, the abovementioned twist is not un-twisted but rather drifts from the center portion of the balloon towards the forward and rearward neck portions. The twist that is drifted towards the rearward neck portion tightens around the wire 106 while moving rearwardly, until it reaches the end element 108 at the forward edge of catheter tube 102, where it is stopped by the diameter stiff increase of the tube relative to the wire. The twist therefore tightens around and against forward-facing aperture 116, thereby at least partially blocking it and preventing sufficient further inflation of balloon 130. Accordingly, the inflation of the conventional catheter shown in stages A'-D' may not provide full inflation of balloon 130 within a body cavity or cylindrical tube, thereby preventing anchoring of balloon 130 to such body cavity or cylindrical tube.

Typically, when a first portion of balloon 130 is twisted about elongate axis 103 relative to a second portion of balloon 130 by at least 720 degrees, a twist will develop as described hereinabove that will at least partially seal the forward-facing aperture 116. Accordingly, the plurality of inflation side apertures 160 is being configured to provide inflation of the balloon 130 therethrough when at least a first portion of the balloon is twisted about elongate axis 103 relative to at least a second portion of the balloon by at least 720 degrees, thereby at least partially sealing forward-facing aperture 116.

Stage D is a final inflation state, wherein pressurized air fills the interior of balloon 130. In Stage D' however pressurized air can only enter the interior of balloon 130 through aperture 116 and aperture 116 is seen to be blocked, thereby preventing full inflation of balloon 130.

Reference is now made to FIGS. 3A & 3B, which are simplified illustrations of a balloon catheter constructed and operative in accordance with another preferred embodiment of the present invention in respective inflated and deflated states.

As seen in FIGS. 3A & 3B, there is a balloon catheter assembly 200 including an elongate catheter tube 202, here shown extending axially along a longitudinal axis 203 and including a lumen 204 having a lumen cross sectional area 205, here also termed a first cross-sectional area. A wire 206, typically formed of stainless steel or nitinol, extends through the catheter tube 202. A wire retraction limiting element 207 is fixedly mounted onto wire 206 for limiting the extent to which wire 206 can retract. An end element 208, preferably having a smoothly rounded apertured front face surface 210, is mounted interiorly and forwardly of a forward edge 212 of catheter tube 202 and defines an inner, generally circular cylindrical surface 214 having a end element cross-sectional area 215, here also termed a second cross-sectional area.

Preferably wire 206 extends through a forward-facing aperture 216 and wire retraction limiting element 207 is configured so as not to be able to pass through aperture 216, thereby limiting the retraction of wire 206 into tube 202. The cross-sectional area of wire 206, here designated by reference numerl 217, is preferably substantially less than the end element cross-sectional area 215. The end element cross-sectional area 215 at aperture 216 minus the cross-sectional area 217 of wire 206 defines a forward inflation cross-sectional area 218, here also termed a third cross-sectional area.

Typical radial dimensions of the first and second cross-sectional areas referenced above are as follows:

First cross-sectional area 205—Diameter preferably between 1-2 mm, more preferably between 1.2-1.8 mm and most preferably between 1.4-1.8 mm.

Second cross-sectional area 215—Diameter preferably between 0.5-1.8 mm, more preferably between 0.8-1.7 mm and most preferably between 1.2-1.6 mm.

Diameter of wire 106 is preferably between 0.3-1 mm, more preferably between 0.35-0.8 mm, and most preferably between 0.4-0.7 mm.

Typical area dimensions of the first, second and third cross-sectional areas referenced above are as follows:

First cross-sectional area 205—Preferably between 0.75-3 mm$^2$, more preferably between 1.1-2.5 mm$^2$, and most preferably between 1.5-2.5 mm$^2$, Second cross-sectional area 215—Preferably between 0.2-2.5 mm$^2$, more preferably between 0.5-2.2 mm$^2$, and most preferably between 1.1-2 mm$^2$, Third cross-sectional area 218—Preferably between 0.1-2.4 mm$^2$, more preferably between 0.3-2 mm$^2$, and most preferably between 0.5-1.8 mm$^2$, Typical ratios between the first, second and third cross-sectional areas are as follows:

The second cross-sectional area 215 is preferably between 30-95% of the first cross-sectional area 205, more preferably between 50-90% of the first cross-sectional sectional area 205 and most preferably between 65-85% of the first cross-sectional area 205.

The third cross-sectional area 218 is preferably between 25-90% of the first cross-sectional area 205, more preferably between 40-85% of the first cross-sectional area 205 and most preferably between 60-80% of the first cross-sectional area 205.

In the orientation shown in FIG. 3A, wire 206 is in its maximal forward extent H, denoted in FIG. 3A by reference numeral 219. Accordingly, the maximal retraction extent of wire 206 through tube 202 is H, as wire retraction limiting element 207 cannot retract rearwardly of aperture 216. Thus, the axial amplitude of extension-retraction of wire 206 through tube 202 is H. H is preferably between 3-16 mm, more preferably between 5-13 mm, and most preferably between 6-10 mm.

Preferably a forward catheter tip 220 is fixed to a forward end of wire 206. A generally non-stretchable inflatable balloon 230 is preferably sealingly fixed at a forward neck portion 232 thereof to a corresponding cylindrical portion 234 of tip 220, as by an adhesive layer 236. Inflatable balloon 230 is preferably sealingly fixed at a rearward neck portion 238 thereof to an outer surface portion 240 of catheter tube 202, as by an adhesive layer 242.

A forward-facing edge 244 of adhesive layer 242 preferably lies at a rearward balloon mounting distance 250 rearwardly of aperture 216, preferably between 5-50 mm. A rearward-facing edge 254 of adhesive layer 236 is separated from the forward-facing edge 244 of outer surface portion 240 by an overall balloon length distance OBLD, here designated by reference numeral 256, which is preferably between 50-140 mm.

Preferably balloon 230, when inflated to a free-shape pressure, typically 5-10 mbar, has a maximum radius RAFSP, here designated by reference 258, which is preferably between 30-70 mm, and more preferably between 35-65 mm. Preferably the ratio between RAFSP and OBLD (namely RAFSP/OBLD) is higher than 0.4, and more preferably this ratio is between 0.5-1.

It is a particular feature of the present invention that the catheter tube 202 is formed with a plurality of balloon inflation side apertures 260 communicating with lumen 204, the plurality of balloon inflation apertures including at least two apertures being arranged at different azimuthal locations along the catheter tube 202 underlying balloon 230. All of apertures 260 have a total aperture cross sectional area which preferably exceeds the third cross sectional area 218 and more preferably exceeds the first cross-sectional area 205.

The total aperture cross sectional area of side apertures 260 is preferably greater than 1.3 times the forward inflation cross-sectional area 218, more preferably greater than 1.7 times the forward inflation cross-sectional area 218, and most preferably greater than 2 times the forward inflation cross-sectional area 218. In accordance with a preferred configuration of side apertures 260, the total aperture cross sectional area of side apertures 260 is not more than 4 times the lumen cross sectional area 205.

The total aperture cross sectional area of side apertures 260 is preferably greater than 1.2 times the lumen cross sectional area 205, more preferably greater than 1.5 times the lumen cross sectional area 205, and most preferably greater than 2 times the lumen cross sectional area 205. In accordance with a yet preferred configuration of side apertures 260, the total aperture cross sectional area of side apertures 260 is not more than 5 times the lumen cross sectional area 205.

It is appreciated that providing a large total aperture cross sectional area of side apertures 260 allows reduced resistance to fluid passage through side apertures 260 and faster inflation and deflation of balloon 230 through lumen 204 of tube 202. It is also appreciated that limiting the total aperture cross sectional area of side apertures 260 to be not greater than 4 times the lumen cross sectional area 205, may be beneficial for maintaining the mechanical strength of the front portion of tube 202 underlying balloon 230.

In the illustrated embodiment, a total of ten balloon inflation side apertures 260 are provided. A preferred arrangement, illustrated in FIGS. 1A & 1B includes two mutually oppositely directed rows 262 and 264 of three apertures 260 each and two mutually oppositely directed rows 266 and 268 of two apertures 260 each, wherein each of rows 262 and 264 is azimuthally offset relative to axis 203 from an adjacent one of rows 266 and 268 by approximately 90 degrees and further wherein each of the apertures 260 in rows 266 and 268 is located axially along axis 203 intermediate and generally equidistant between each pair of adjacent apertures 260 in rows 262 and 264.

It is a further particular feature of the present invention that the balloon is characterized by having an inflated state and a corresponding deflated state wherein at least a first portion of the balloon is capable of being twisted relative to at least a second portion of the balloon, resulting in at least partial blockage of at least one but not all of the plurality of the balloon side apertures 260. The wire retraction limiting element 207 limits the retraction of wire 206 into tube 202 when the balloon is twisted.

Reference is now made to FIG. 4, which is a simplified illustration of stages A, B, C & D of inflation of the balloon catheter of FIGS. 3A & 3B.

Stage A shows the balloon catheter of FIGS. 3A & 3B in a fully deflated twisted state.

Stage B is an initial inflation state, wherein pressurized air enters the interior of balloon 230 through apertures 216 and 260.

Stage C is a further inflation state, wherein pressurized air continues to enter the interior of balloon 230 through apertures 216 and 260.

Stage D is a final inflation state, wherein pressurized air fills the interior of balloon 230.

Reference is now made to FIGS. 5A & 5B, which are simplified illustrations of a balloon catheter constructed and operative in accordance with yet another preferred embodiment of the present invention in respective inflated and deflated states.

As seen in FIGS. 5A & 5B, there is a balloon catheter assembly 300 including an elongate catheter tube 302, here shown extending axially along a longitudinal axis 303 and including a lumen 304 having a lumen cross sectional area 305, here also termed a first cross-sectional area. A wire 306, typically formed of stainless steel or nitinol, extends through the catheter tube 302. A wire retraction limiting element 307 is fixedly mounted onto wire 306 for limiting the extent to which wire 306 can retract. An end element 308, preferably having a smoothly rounded apertured front face surface 310, is mounted interiorly and forwardly of a forward edge 312 of catheter tube 302 and defines an inner, generally circular cylindrical surface 314 having a end element cross-sectional area 315, here also termed a second cross-sectional area.

Preferably wire 306 extends through a forward-facing aperture 316. The cross-sectional area of wire 306, here designated by reference numeral 317, is preferably substantially less than the end element cross-sectional area 315. The cross-sectional area of wire retraction limiting element 307 is larger than that of aperture 316, thereby limiting the extent to which wire 306 can retract. The end element cross-sectional area 315 at aperture 316 minus the cross-sectional area 317 of wire 306 defines a forward inflation cross-sectional area 318, here also termed a third cross-sectional area.

Typical radial dimensions of the first and second cross-sectional areas referenced above are as follows:

First cross-sectional area 305—Diameter preferably between 1-2 mm, more preferably between 1.2-1.8 mm and most preferably between 1.4-1.8 mm.

Second cross-sectional area 315—Diameter preferably between 0.5-1.8 mm, more preferably between 0.8-1.7 mm and most preferably between 1.2-1.6 mm.

Diameter of wire 306 is preferably between 0.3-1 mm, more preferably between 0.35-0.8 mm, and most preferably between 0.4-0.7 mm.

Typical area dimensions of the first, second and third cross-sectional areas referenced above are as follows:

First cross-sectional area 305—Preferably between 0.75-3 $mm^2$, more preferably between 1.1-2.5 $mm^2$, and most preferably between 1.5-2.5 $mm^2$, Second cross-sectional area 315—Preferably between 0.2-2.5 $mm^2$, more preferably between 0.5-2.2 $mm^2$, and most preferably between 1.1-2 $mm^2$, Third cross-sectional area 318—Preferably between 0.1-2.4 $mm^2$, more preferably between 0.3-2 $mm^2$, and most preferably between 0.5-1.8 $mm^2$, Typical ratios between the first, second and third cross-sectional areas are as follows:

The second cross-sectional area 315 is preferably between 30-95% of the first cross-sectional area 305, more preferably between 50-90% of the first cross-sectional area 305 and most preferably between 65-85% of the first cross-sectional area 305.

The third cross-sectional area 318 is preferably between 25-90% of the first cross-sectional area 305, more preferably between 40-85% of the first cross-sectional area 305 and most preferably between 60-80% of the first cross-sectional area 305.

In the orientation shown in FIG. 5A, wire 306 is in its maximal forward extent H, also referred to as the second distance, denoted in FIG. 5A by reference numeral 319. Accordingly, the maximal retraction extent of wire 306 through tube 302 is H, as wire retraction limiting element 307 cannot retract rearwardly of aperture 316. Thus, the axial amplitude of extension-retraction of wire 306 through tube 302 is H. H is preferably between 3-16 mm, more preferably between 5-13 mm, and most preferably between 6-10 mm.

Preferably a forward catheter tip 320 is fixed to a forward end of wire 306. A generally non-stretchable inflatable balloon 330 is preferably sealingly fixed at a forward neck portion 332 thereof to a corresponding cylindrical portion 334 of tip 320, as by an adhesive layer 336. Inflatable balloon 330 is preferably sealingly fixed at a rearward neck portion 338 thereof to an outer surface portion 340 of catheter tube 302, as by an adhesive layer 342.

A forward-facing edge 344 of adhesive layer 342 preferably lies at a rearward balloon mounting distance 350 rearwardly of aperture 316, preferably between 5-50 mm. A rearward-facing edge 354 of adhesive layer 336 is separated from the forward-facing edge 344 of outer surface portion 340 by an overall balloon length distance OBLD, here designated by reference numeral 356, which is preferably between 50-140 mm.

Preferably balloon 330, when inflated to a free-shape pressure, typically 5-10 mbar, has a maximum radius RAFSP, here designated by reference 358, which is preferably between 30-70 mm, and more preferably between 35-65 mm. Preferably the ratio between RAFSP and OBLD (namely RAFSP/OBLD) is higher than 0.4, and more preferably this ratio is between 0.5-1.

It is a particular feature of the present invention that the catheter tube 302 is formed with a plurality of balloon inflation side apertures 360 communicating with lumen 304, the plurality of balloon inflation apertures including at least two apertures being arranged at different azimuthal locations along the catheter tube 302 underlying balloon 330. All of apertures 360 have a total aperture cross sectional area which preferably exceeds the third cross sectional area 318 and more preferably exceeds the first cross-sectional area 305.

The total aperture cross sectional area of side apertures 360 is preferably greater than 1.3 times the forward inflation cross-sectional area 318, more preferably greater than 1.7 times the forward inflation cross-sectional area 318, and most preferably greater than 2 times the forward inflation cross-sectional area 318. In accordance with a preferred configuration of side apertures 360, the total aperture cross sectional area of side apertures 360 is not more than 4 times the lumen cross sectional area 305.

The total aperture cross sectional area of side apertures 360 is preferably greater than 1.2 times the lumen cross sectional area 305, more preferably greater than 1.5 times the lumen cross sectional area 305, and most preferably greater than 2 times the lumen cross sectional area 305. In accordance with a yet preferred configuration of side apertures 360, the total aperture cross sectional area of side apertures 360 is not more than 5 times the lumen cross sectional area 305.

It is appreciated that providing a large total aperture cross sectional area of side apertures 360 allows reduced resistance to fluid passage through side apertures 360 and faster inflation and deflation of balloon 330 through lumen 304 of tube 302. It is also appreciated that limiting the total aperture cross sectional area of side apertures 360 to be not greater than 4 times the lumen cross sectional area 305, may be beneficial for maintaining the mechanical strength of the front portion of tube 302 underlying balloon 330.

In the illustrated embodiment, a total of ten balloon inflation side apertures 360 are provided. A preferred arrangement, illustrated in FIGS. 5A & 5B includes two mutually oppositely directed rows 362 and 364 of three apertures 360 each and two mutually oppositely directed rows 366 and 368 of two apertures 360 each, wherein each of rows 362 and 364 is azimuthally offset relative to axis 303 from an adjacent one of rows 366 and 368 by approximately 90 degrees and further wherein each of the apertures 360 in rows 366 and 368 is located axially along axis 303 intermediate and generally equidistant between each pair of adjacent apertures 360 in rows 362 and 364.

It is a further particular feature of the present invention that the balloon is characterized by having an inflated state and a corresponding deflated state wherein at least a first portion of the balloon is capable of being twisted relative to at least a second portion of the balloon, resulting in at least partial blockage of at least one but not all of the plurality of the balloon side apertures 360.

In the embodiment of FIGS. 5A & 5B, twisting of balloon 330 may be intentionally effected by furling balloon 330 over wire 306, which is beneficial for reducing the cross-sectional diameter of balloon 330 in a deflated state, thereby enabling its insertion through an instrument channel of an endoscope, as described in detail in Applicant's published PCT patent application number WO2010/137025, the disclosure of which is hereby incorporated by reference.

As seen in FIGS. 5A & 5B, a furling assembly 380 is connected to catheter tube 302 and wire 306 at a rearward portion thereof, and is operative to provide user-selectable furling and unfurling of wire 306 with respect to tube 302, azimuthally around longitudinal axis 303 as denoted by arrow 386. Furling assembly 380 may be identical to the furling assembly described in detail in Applicant's published PCT patent application number WO2010/137025, the disclosure of which is hereby incorporated by reference.

It is appreciated that furling of balloon 330 around wire 306 causes wire 306 to retract rearwardly through lumen 304 of tube 302, since the balloon 330 forms a spiral arrangement around wire 306, forcing the balloon 330 to assume a longitudinal distance that is shorter than its maximal unfurled extended distance. This rearward axial displacement of the wire 306 relative to tube 302 as a result of the balloon 330 being furled is no greater than a maximal distance relative to said elongate catheter tube, herein referred to as the first distance. The first distance is a function of the maximal furling allowable by furling assembly 380.

It is a particular feature of the present invention that the second distance H is a function of the first distance. In accordance with a preferred embodiment of the present invention, second distance H is longer than the first distance. This construction allows balloon 330 to be untentioned when fully furled, therby reducing forces on balloon 330 and providing higher flexibility of the forward portion of catheter assembly 300. The ratio of the second distance to the first distance in this embodiment is preferably greater than 1.3, more preferably greater than 1.5, and most preferably greater than 2.

In accordance with another preferred embodiment of the present invention, the first distance is longer than second distance H. This construction allows balloon 330 to be tightly furled, thereby allowing its insertion through narrow instrument channels. The ratio of the first distance to the second distance in this embodiment is preferably greater than 1.3, more preferably greater than 1.5, and most preferably greater than 2.

According to a yet preferred configuration of catheter assembly 300, second distance H is preferably in the range of 5-20 millimeters, and more preferably in the range of 6-12 millimeters.

It is appreciated that wire retraction limiting element 307, limits the extent to which wire 306 can retract, is beneficial not only in case of furling-related retraction, but also if the wire is retracted due to forces applied on its forward portion or on forward tip 320, such as during advancement of catheter assembly 300 in a body cavity such as the intestine, during an endoscopic examination. If limiting element 307 would have been obviated and wire 306 was able to retract to a considerable axial extent, then the length of balloon 330 would have been reduced accordingly, thereby causing resistance of balloon 330 to withdrawal through an instrument channel of an endoscope during endoscopic examination, since more balloon material is piled in a shorter axial length. Preferably, limiting element 307 limits the maximal retraction H such that no pile-up of balloon material will occur during withdrawal of catheter assembly 300 through an instrument channel.

FIG. 6A is a simplified illustration of the balloon catheter of FIGS. 5A & 5B in a deflated unfurled fully extended state. It is seen that the wire retraction limiting element 307 is spaced forwardly of aperture 316 by a distance H.

FIG. 6B is a simplified illustration of the balloon catheter of FIGS. 5A & 5B in a deflated unfurled fully retracted state. It is seen that the wire retraction limiting element 307 engages aperture 316 and cannot pass through it, thereby limiting retraction of wire 306 into tube 302.

FIG. 6C is a simplified illustration of the balloon catheter of FIGS. 5A & 5B in a deflated furled state. It is seen that the wire retraction limiting element 307 engages aperture 316 and cannot pass through it, thereby limiting retraction of wire 306 into tube 302.

Reference is now made to FIGS. 7A, 7B, 7C & 7D, which are simplified illustrations of a first embodiment of a balloon endoscope constructed and operative in accordance with a preferred embodiment of the present invention in four inflated orientations.

Figure 7A:
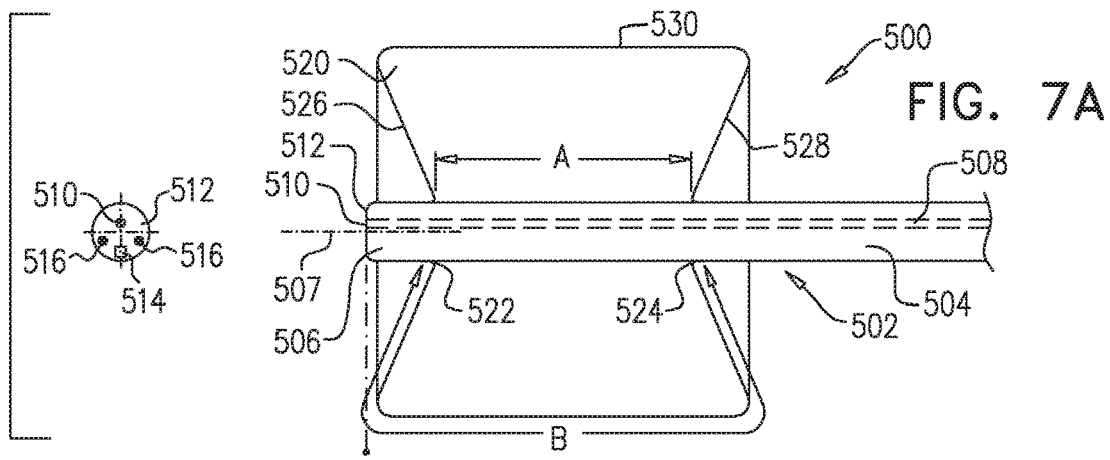
FIGS. 7A, 7B, 7C & 7D are simplified illustrations of a first embodiment of a balloon endoscope constructed and operative in accordance with a preferred embodiment of the present invention in four inflated orientations.

As seen in FIG. 7A, there is provided an anchoring balloon endoscope 500 including an elongate endoscope 502 having an elongate endoscope body portion 504 and a forward end portion 506. The forward end portion 506 and at least a part of the body portion 504 adjacent thereto, extend along a longitudinal axis 507. An instrument channel 508 is typically formed in endoscope body portion 504 and has a forward opening 510 at a forward-facing surface 512 of forward end portion 506. Also located at forward-facing surface 512 of forward end portion 506 are viewing optics 514, such as a CCD camera, and illumination elements 516, such as LEDs.

In accordance with a preferred embodiment of the present invention there is fixedly mounted on the endoscope body 504 adjacent the forward end portion 506, a substantially non-stretchable, inflatable anchoring balloon 520. It is a particular feature of the present invention that the balloon is constructed and operative to be securely anchored in a generally tubular body portion, such as the esophagus but at the same time to allow axial back and forth, forward and backward movement of the forward end portion 506. This apparatus is highly beneficial in endoscopic examination and treatment of diseases of the gastro-esophageal junction.

The substantially non-stretchable, inflatable anchoring balloon 520 may be selectably inflated or deflated via an interior volume of the endoscope as described in Applicant's published PCT patent applications WO2011/111040 and WO/2012/120492, the descriptions of which are hereby incorporated by reference. Alternatively a dedicated inflation/deflation channel, either interior of or exterior to the endoscope body 504 may be employed.

In the illustrated embodiment of FIG. 7A, the substantially non-stretchable, inflatable anchoring balloon 520 inflates to a generally double trapezoidal axial cross sectional free shape at relatively low pressure, such as 5-10 mbar. The balloon is preferably made of any suitable material such as organic or inorganic polymer, nylon or silicone, of thickness typically between 0.01-0.4 mm, and is sealingly mounted onto the endoscope body and anchored at first and second sealing attachment locations 522 and 524, along the elongate endoscope, which are separated by a distance A.

As seen in FIG. 7A, each of the two trapezoidal cross-sectional portions of the double trapezoidal axial cross sectional free shape of the substantially non-stretchable, inflatable anchoring balloon 520 has a balloon surface axial cross-sectional extent B, which includes forwardly and rearwardly facing radially outward extending transverse cross-sectional portions 526 and 528 and a radially displaced cross-sectional portion 530 which is parallel to axis 507 and has a length which is greater than distance A.

Preferably the length of portion 530 is at least 30% greater than distance A, more preferably the length of portion 530 is at least 50% greater than distance A and most preferably the length of portion 530 is at least 100% greater than distance A. Extent B is preferably at least 1.5 times greater than A, more preferably at least 2 times greater than A and most preferably at least 3 times greater than A.

Figure 7B:
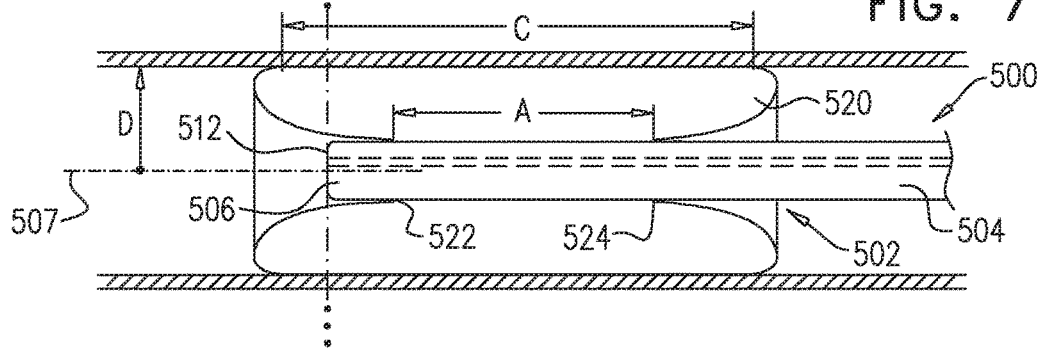

Referring now additionally to FIG. 7B, it is seen that the substantially non-stretchable, inflatable balloon 520, when inflated to an anchoring pressure typically greater than 20 mbar and preferably greater that 60 mbar, within a cylindrical element having an inner radius D that is coaxial with and surrounding at least a portion of the elongate endoscope, has a cylindrical anchoring surface in contact with an inner surface of the cylindrical element. The cylindrical anchoring surface has an axial cross-sectional extent C.

It is a particular feature of the present invention that the following geometrical relationship exists:

A<C<B; and $C-A > m \times D$, where $m \geq 1$.

Preferably m is approximately 1, more preferably m is greater than 1.5 and most preferably m is greater than 2.

It is appreciated that in medical treatment the cylindrical element may be an esophagus of a patient, however the geometrical structure of the balloon 520 defined hereinabove is independent of the nature of the cylindrical element other than its geometry as defined hereinabove, in which case the cylindrical element may be a test fixture.

Figure 7C:
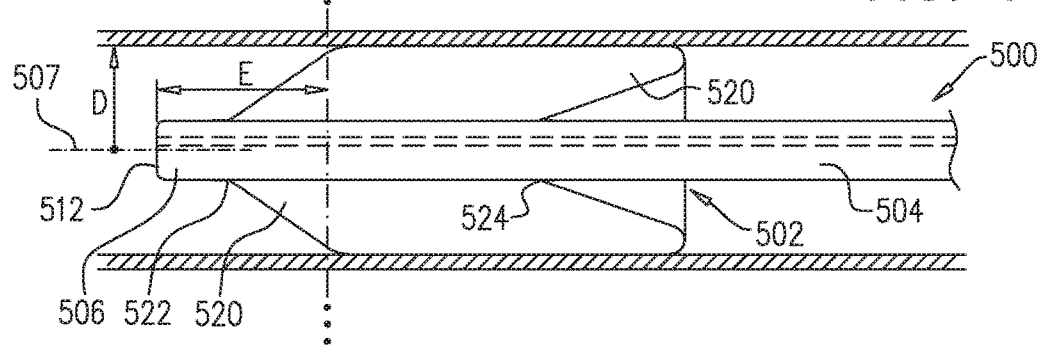

Referring now to FIG. 7C, it is seen that in accordance with a preferred embodiment of the present invention, the endoscope may be readily pushed forwardly along axis 507 while anchored with a maximum forward displacement of E, where:

$E > n \times D$, where $n \geq 1$

Preferably, n is approximately 1, more preferably n is greater than 1.5, and most preferably n is greater than 2.

Figure 7D:
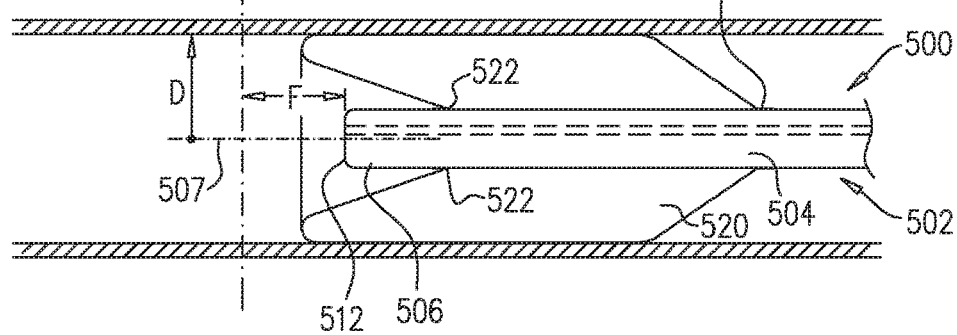

Referring now to FIG. 7D, it is seen that in accordance with a preferred embodiment of the present invention, the endoscope may be readily pushed rearwardly along axis 507 while anchored with a maximum rearward displacement of F, which need not be equal to E and where:

$F > k \times D$, where $k \geq 1$

Preferably, k is approximately 1, more preferably k is greater than 1.5, and most preferably k is greater than 2.

Reference is now made to FIGS. 8A, 8B, 8C & 8D, which are simplified illustrations of a second embodiment of a balloon endoscope constructed and operative in accordance with a preferred embodiment of the present invention in four inflated orientations.

Figure 8A:
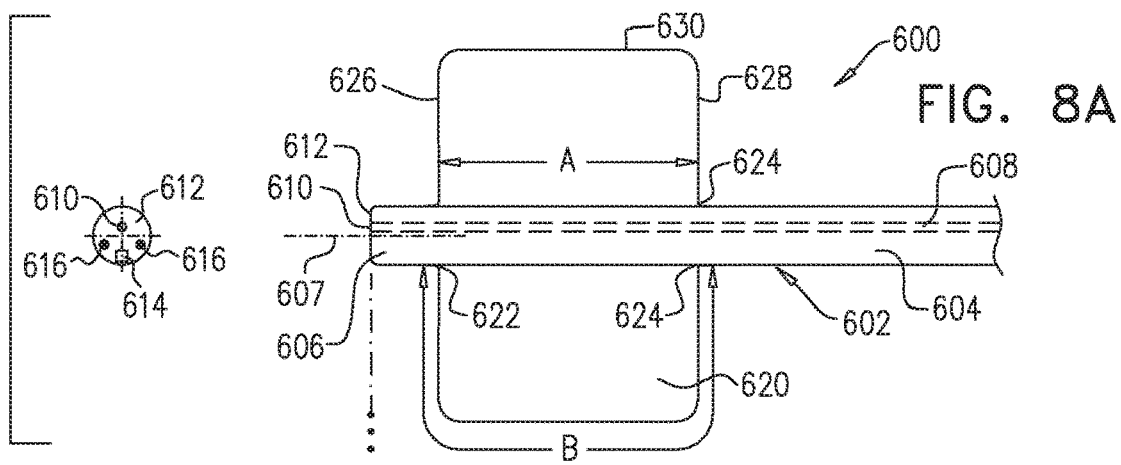
FIGS. 8A, 8B, 8C & 8D are simplified illustrations of a second embodiment of a balloon endoscope constructed and operative in accordance with another preferred embodiment of the present invention in four inflated orientations.

As seen in FIG. 8A, there is provided an anchoring balloon endoscope 600 including an elongate endoscope 602 having an elongate endoscope body portion 604 and a forward end portion 606. The forward end portion 606 and at least a part of the body portion 604 adjacent thereto, extend along a longitudinal axis 607. An instrument channel 608 is typically formed in endoscope body portion 604 and has a forward opening 610 at a forward-facing surface 612 of forward end portion 606. Also located at forward-facing surface 612 of forward end portion 606 are viewing optics 614, such as a CCD camera, and illumination elements 616, such as LEDs.

In accordance with a preferred embodiment of the present invention there is fixedly mounted on the endoscope body 604 adjacent the forward end portion 606, a substantially non-stretchable, inflatable anchoring balloon 620. It is a particular feature of the present invention that the balloon is constructed and operative to be securely anchored in a generally tubular body portion, such as the esophagus but at the same time to allow axial back and forth, forward and backward movement of the forward end portion 606. This apparatus is highly beneficial in endoscopic examination and treatment of diseases of the gastro-esophageal junction.

The substantially non-stretchable, inflatable anchoring balloon 620 may be selectably inflated or deflated via an interior volume of the endoscope as described in Applicant's published PCT patent applications WO2011/111040 and WO/2012/120492, the descriptions of which are hereby incorporated by reference. Alternatively a dedicated inflation/deflation channel, either interior of or exterior to the endoscope body 604 may be employed.

In the illustrated embodiment of FIG. 8A, the substantially non-stretchable, inflatable anchoring balloon 620 inflates to a generally double rectangular axial cross sectional free shape at relatively low pressure, such as 5-10 mbar. The balloon is preferably made of any suitable material such as organic or inorganic polymer, nylon or silicone, of thickness typically between 0.01-0.4 mm, and is sealingly mounted onto the endoscope body at anchored at first and second sealing attachment locations 622 and 624, along the elongate endoscope, which are separated by a distance A.

As seen in FIG. 8A, each of the two rectangular cross-sectional portions of the double rectangular axial cross sectional free shape of the substantially non-stretchable, inflatable anchoring balloon 620 has a balloon surface axial cross-sectional extent B, which includes forwardly and rearwardly facing radially outward extending transverse cross-sectional portions 626 and 628 and a radially displaced cross-sectional portion 630 which is parallel to axis 607 and has a length which is greater than distance A.

Preferably the length of portion 630 is at least 30% greater than distance A, more preferably the length of portion 630 is at least 50% greater than distance A and most preferably the length of portion 630 is at least 100% greater than distance A. Extent B is preferably at least 1.5 times greater than A, more preferably at least 2 times greater than A and most preferably at least 3 times greater than A.

Figure 8B:
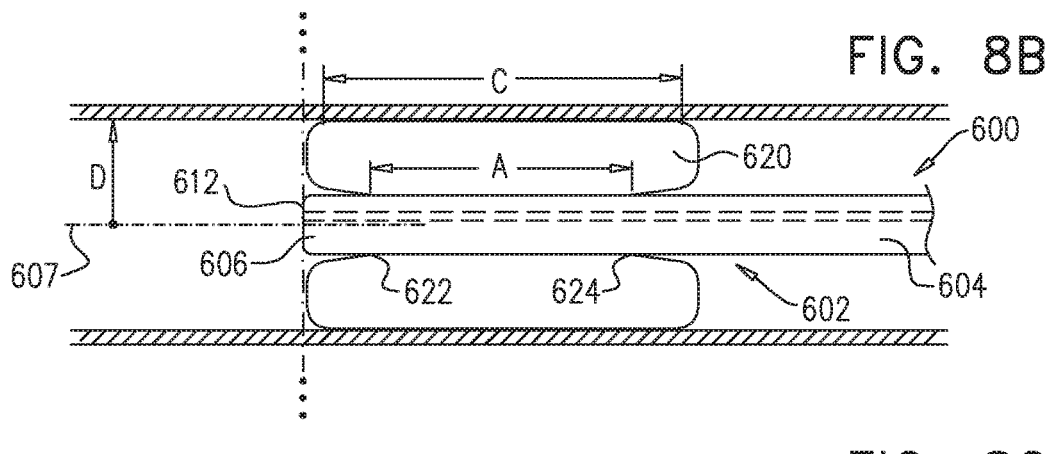

Referring now additionally to FIG. 8B, it is seen that the substantially non-stretchable, inflatable balloon 620, when inflated to an anchoring pressure typically greater than 20 mbar and preferably greater that 60 mbar, within a cylindrical element having an inner radius D that is coaxial with and surrounding at least a portion of the elongate endoscope, has a cylindrical anchoring surface in contact with an inner surface of the cylindrical element. The cylindrical anchoring surface has an axial cross-sectional extent C.

It is a particular feature of the present invention that the following geometrical relationship exists:

$A<C<B$; and $C-A>m\times D$, where $m\geq 1$.

Preferably m is 1, more preferably, m is greater than 1.5 and most preferably m is greater than 2.

It is appreciated that in medical treatment the cylindrical element may be an esophagus of a patient, however the geometrical structure of the balloon 620 defined hereinabove is independent of the nature of the cylindrical element other than its geometry as defined hereinabove, in which case the cylindrical element may be a test fixture.

Figure 8C:
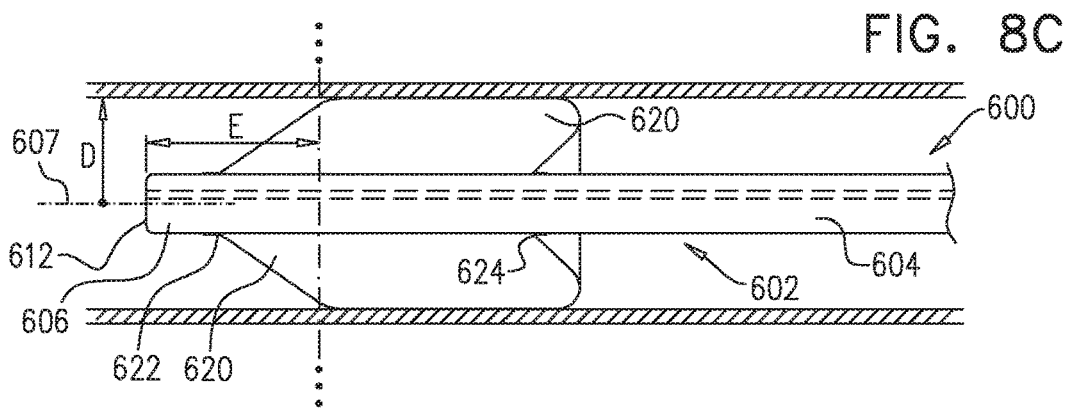

Referring now to FIG. 8C, it is seen that in accordance with a preferred embodiment of the present invention, the endoscope may be readily pushed forwardly along axis 607 while anchored with a maximum forward displacement of E, where:

$E>n\times D$, where $n\geq 1$

Preferably, n is approximately 1, more preferably n is greater than 1.5, and most preferably n is greater than 2.

Figure 8D:
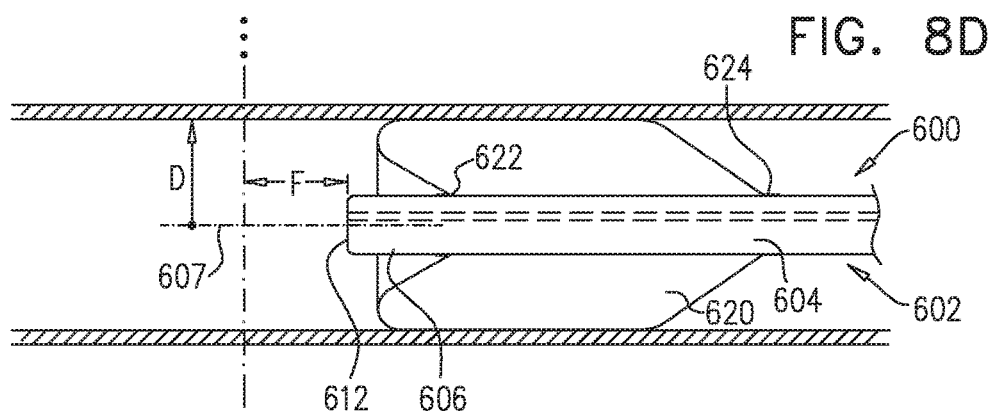

Referring now to FIG. 8D, it is seen that in accordance with a preferred embodiment of the present invention, the endoscope may be readily pushed rearwardly along axis 607 while anchored with a maximum rearward displacement of F, which need not be equal to E and where:

$F\geq k\times D$, where $k\geq 1$

Preferably, k is approximately 1, more preferably k is greater than 1.5, and most preferably k is greater than 2.

Reference is now made to FIGS. 9A, 9B, 9C & 9D, which are simplified illustrations of a third embodiment of a balloon endoscope constructed and operative in accordance with a preferred embodiment of the present invention in four inflated orientations.

Figure 9A:
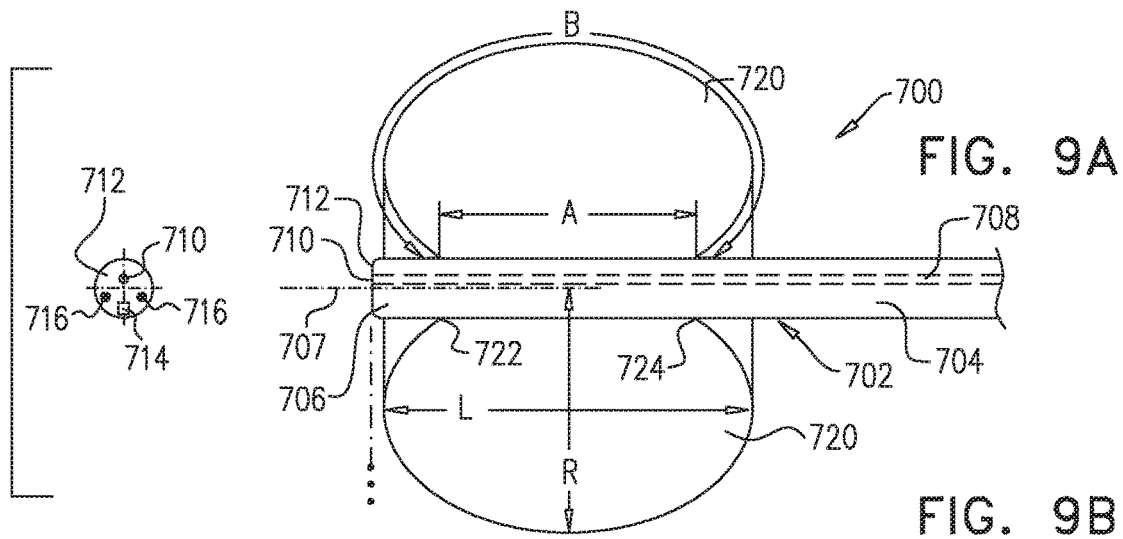
FIGS. 9A, 9B, 9C & 9D are simplified illustrations of a third embodiment of a balloon endoscope constructed and operative in accordance with another preferred embodiment of the present invention in four inflated orientations.

As seen in FIG. 9A, there is provided an anchoring balloon endoscope 700 including an elongate endoscope 702 having an elongate endoscope body portion 704 and a forward end portion 706. The forward end portion 706 and at least a part of the body portion 704 adjacent thereto, extend along a longitudinal axis 707. An instrument channel 708 is typically formed in endoscope body portion 704 and has a forward opening 710 at a forward-facing surface 712 of forward end portion 706. Also located at forward-facing surface 712 of forward end portion 706 are viewing optics 714, such as a CCD camera, and illumination elements 716, such as LEDs.

In accordance with a preferred embodiment of the present invention there is fixedly mounted on the endoscope body 704 adjacent the forward end portion 706, a substantially non-stretchable, inflatable anchoring balloon 720. It is a particular feature of the present invention that the balloon is constructed and operative to be securely anchored in a generally tubular body portion, such as the esophagus, but at the same time to allow axial back and forth, forward and backward movement of the forward end portion 706. This apparatus is highly beneficial in endoscopic examination and treatment of diseases of the gastro-esophageal junction.

The substantially non-stretchable, inflatable anchoring balloon 720 may be selectably inflated or deflated via an interior volume of the endoscope as described in Applicant's published PCT patent applications WO2011/111040 and WO/2012/120492, the descriptions of which are hereby incorporated by reference. Alternatively a dedicated inflation/deflation channel, either interior of or exterior to the endoscope body 704 may be employed.

In the illustrated embodiment of FIG. 9A, the substantially non-stretchable, inflatable anchoring balloon 720 inflates to a generally double elliptical axial cross sectional free shape at relatively low pressure, such as 5-10 mbar. The balloon is preferably made of any suitable material such as organic or inorganic polymer, nylon or silicone, of thickness typically between 0.01-0.4 mm, and is sealingly mounted onto the endoscope body at anchored at first and second sealing attachment locations 722 and 724, along the elongate endoscope, which are separated by a distance A.

As seen in FIG. 9A, each of the two elliptical cross-sectional portions of the double elliptical axial cross sectional free shape of the substantially non-stretchable, inflatable anchoring balloon 720 has a balloon surface axial cross-sectional extent B, a maximal longitudinal extent L and a maximal radial extent R. Preferably, balloon surface axial cross-sectional extent B is greater than distance A. Yet preferably, longitudinal extent L is greater than distance A. In accordance with a preferred embodiment of the present invention, the ratio between radial extent R and distance A is in the range of 0.8-1.6, and more preferably in the range of 1.0-1.6.

Figure 9B:
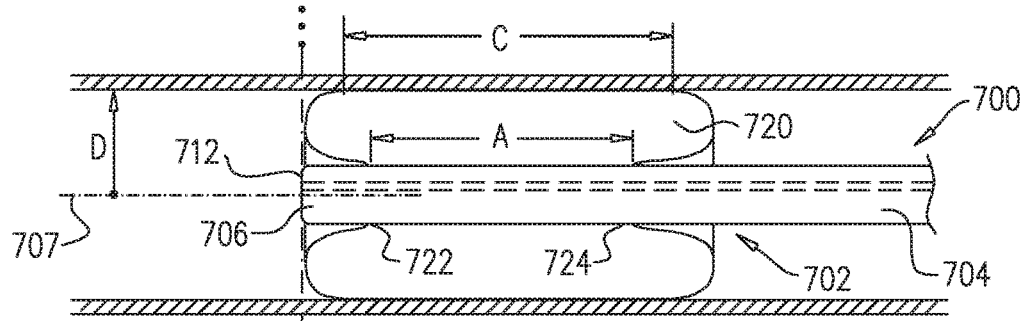

Extent B is preferably at least 1.5 times greater than A, more preferably at least 2 times greater than A and most preferably at least 3 times greater than A. Referring now additionally to FIG. 9B, it is seen that the substantially non-stretchable, inflatable balloon 720, when inflated to an anchoring pressure typically greater than 20 mbar and preferably greater that 60 mbar, within a cylindrical element having an inner radius D that is coaxial with and surrounding at least a portion of the elongate endoscope, has a cylindrical anchoring surface in contact with an inner surface of the cylindrical element. The cylindrical anchoring surface has an axial cross-sectional extent C.

It is a particular feature of the present invention that the following geometrical relationship exists:

$A<C<B$; and $C-A>m\times D$, where $m\geq 1$.

Preferably m is 1, more preferably, m is greater than 1.5 and most preferably m is greater than 2.

It is appreciated that in medical treatment the cylindrical element may be an esophagus of a patient, however the geometrical structure of the balloon 720 defined hereinabove is independent of the nature of the cylindrical element other than its geometry as defined hereinabove, in which case the cylindrical element may be a test fixture.

Figure 9C:
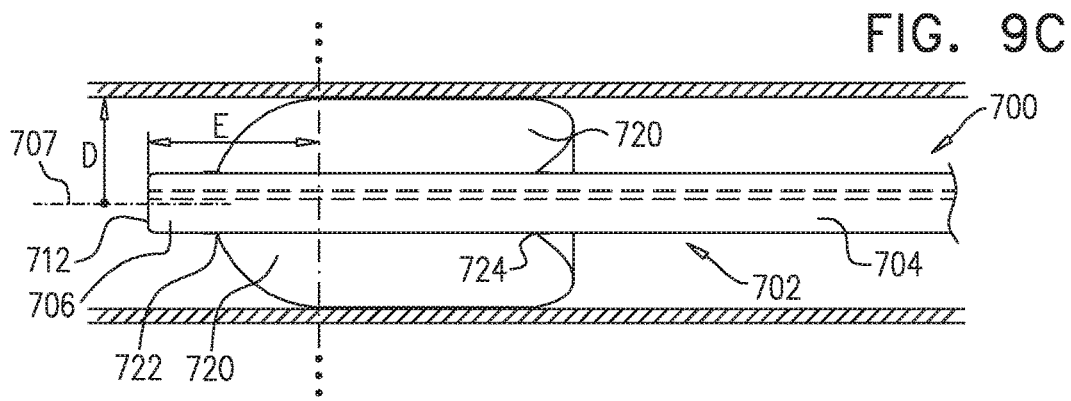

Referring now to FIG. 9C, it is seen that in accordance with a preferred embodiment of the present invention, the endoscope may be readily pushed forwardly along axis 707 while anchored with a maximum forward displacement of E, where:

$E>n\times D$, where $n\geq 1$

Preferably, n is approximately 1, more preferably n is greater than 1.5, and most preferably n is greater than 2.

Figure 9D:
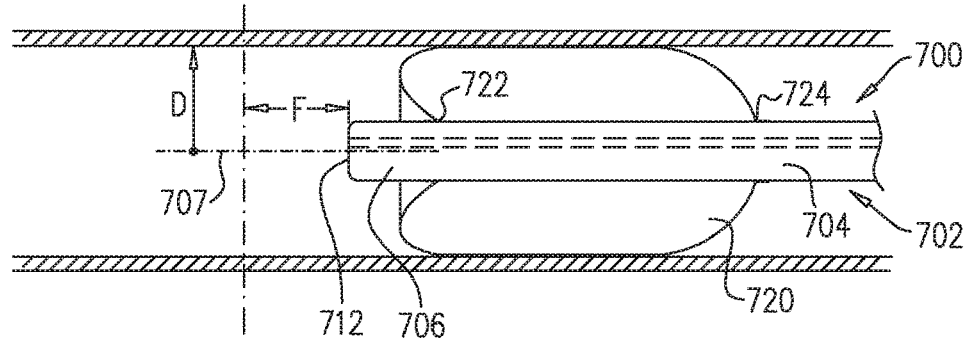

Referring now to FIG. 9D, it is seen that in accordance with a preferred embodiment of the present invention, the endoscope may be readily pushed rearwardly along axis 707 while anchored with a maximum rearward displacement of F, which need not be equal to E and where:

$F>k\times D$, where $k\geq 1$

Preferably, k is approximately 1, more preferably k is greater than 1.5, and most preferably k is greater than 2.

Reference is now made to FIGS. 10A, 10B, 10C, 10D, 10E, 10F, 10G, 10H, 10I and 10J, which are simplified illustrations of one clinical application of the balloon endoscope of any of FIGS. 7A-9D, here specifically for treatment of Barrett's Esophagus disorder. For the sake of simplicity and conciseness, the reference numerals which appear in the description which follows are not those which appear in the above descriptions of FIGS. 7A-9D, it being understood that they may correspond to elements in any of the three different embodiments shown in FIGS. 7A-7D, 8A-8D and 9A-9D.

Figure 10C:
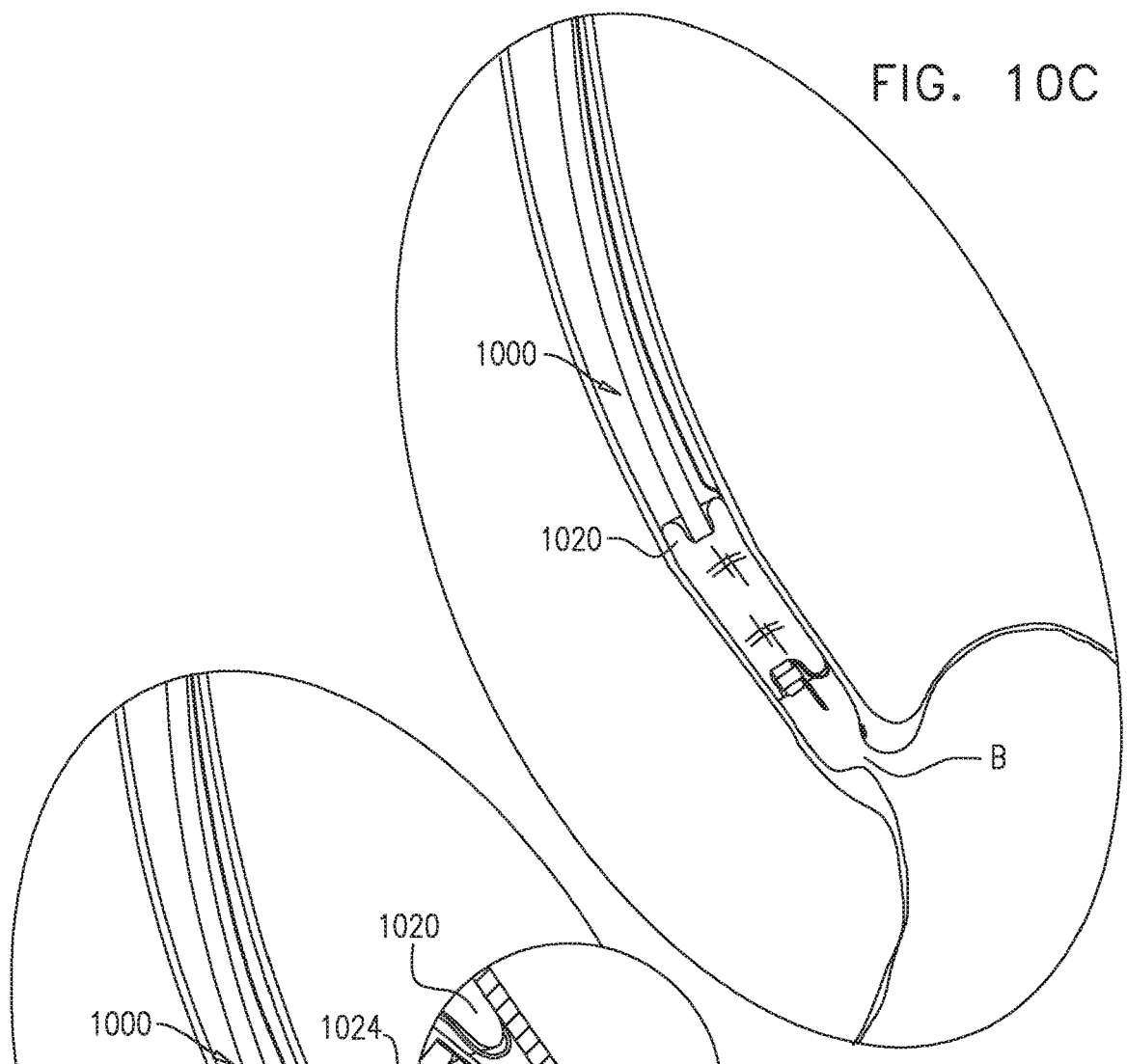

Turning to FIG. 10A, it is seen that an anchoring balloon endoscope 1000 is initially inserted orally into the esophagus of a patient, as in routine gastroscopy, with an anchoring balloon 1020 in a deflated state. A therapeutic or diagnostic device is mounted onto a forward tip 1024 of endoscope 1000. In the example of FIGS. 10A-10J, device 1022 is an ablation device, such as a Model Barrx™ 90 RFA Focal Catheter, commercially available from Covidien of 540 Oakmead Parkway, Sunnyvale, Calif. 94085, USA, which is mounted onto a forward tip 1024 of endoscope 1000 and is operative to ablate and peel off a Barrett pathology, indicated by reference letter A, in FIG. 10A, which is located in the esophagus or stomach of the patient, adjacent the gastro-esophageal valve, which is indicated by reference letter B, in FIG. 10A.

FIG. 10B shows further advancement of the anchoring balloon endoscope 1000 in the esophagus of the patient until the ablation device is located in proximity to the Barrett pathology A and the gastro-esophageal valve B.

FIG. 10C shows inflation of anchoring balloon 1020 in the esophagus, thereby anchoring the endoscope 1000 in the esophagus and radially stabilizing it with respect to the esophagus.

Figure 10D:
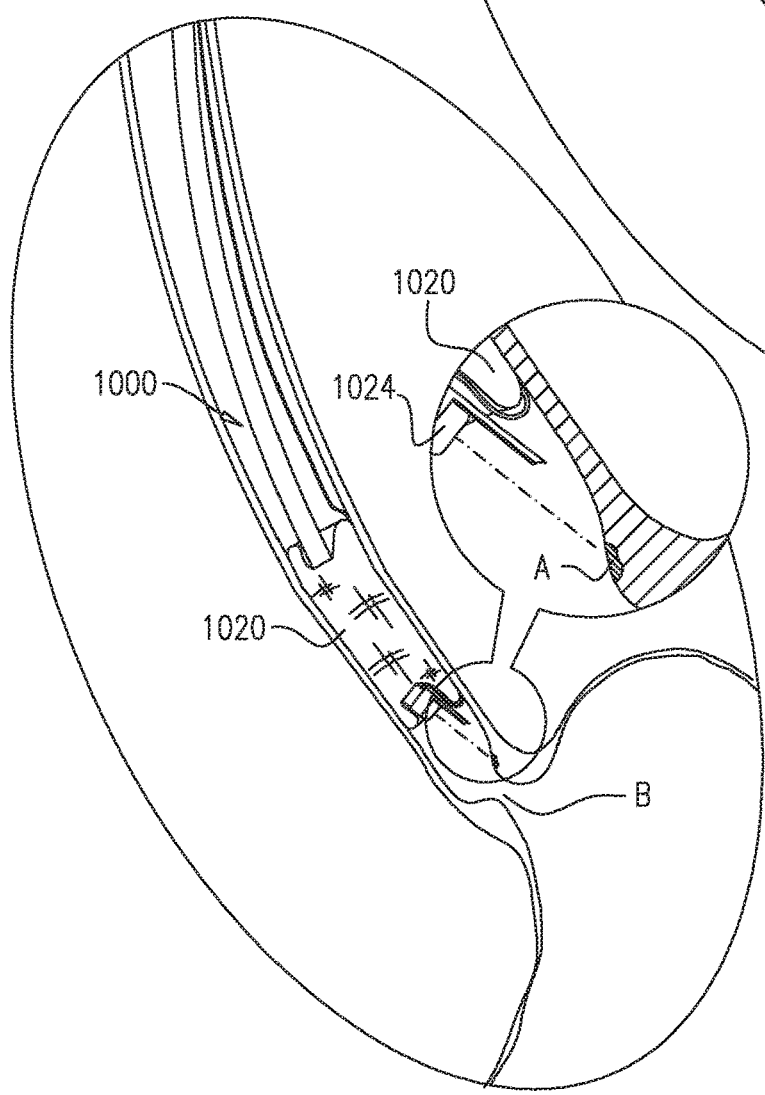

FIG. 10D shows sideways deflection of the forward tip 1024 of the endoscope 1000, allowing forward-looking optics (not shown) mounted on tip 1024 to detect a pathology, in this example the Barrett pathology A, adjacent the gastro-esophageal valve B.

Figure 10E:
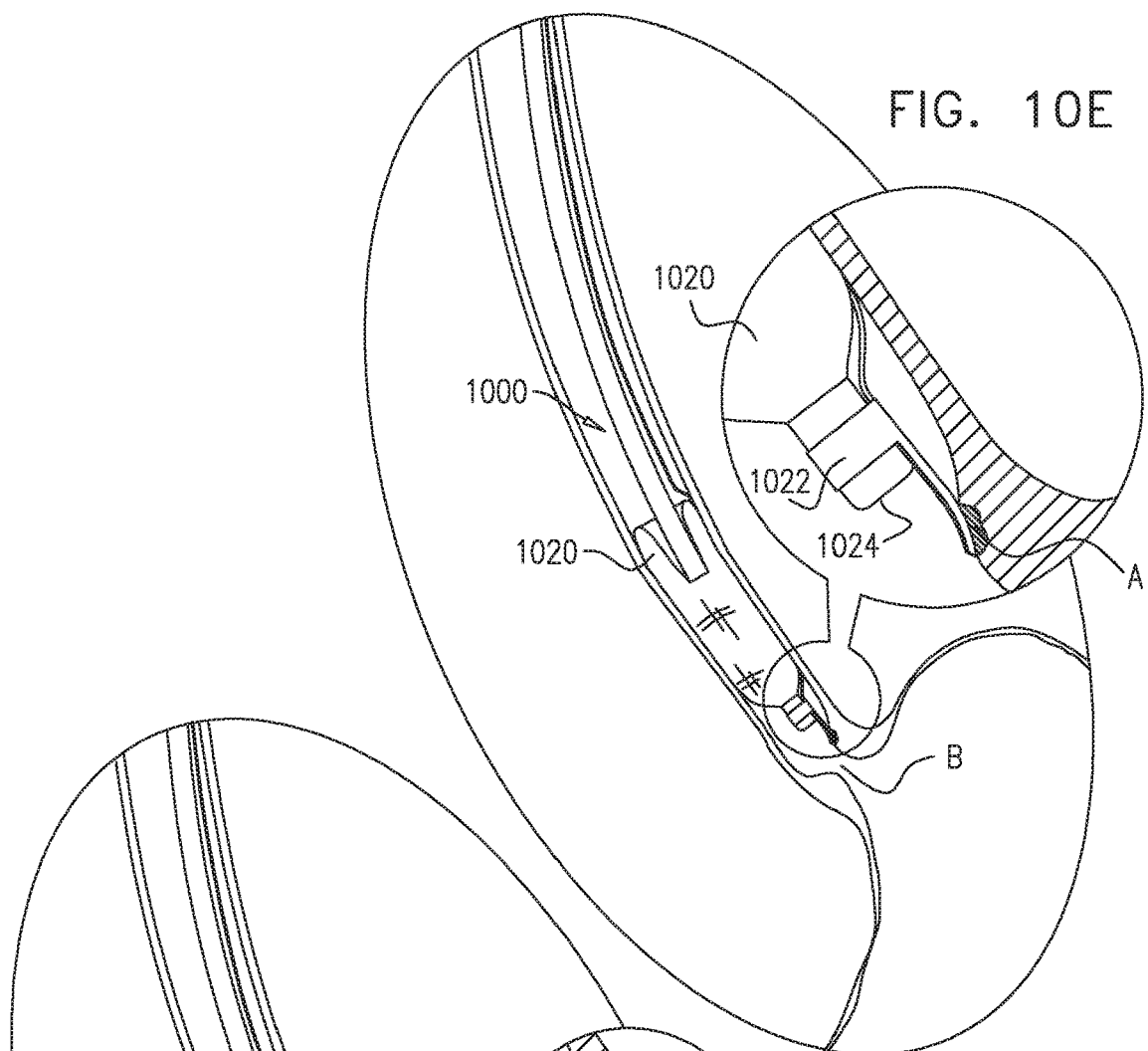

FIG. 10E shows a particular feature of the endoscope of any of the embodiments shown in FIGS. 7A-7D, 8A-8D and 9A-9D, whereby the endoscope 1000 is pushed forwardly while being anchored by the balloon 1020, thereby positioning the ablation device 1022 in operative engagement with the Barrett pathology A and enabling ablation of the pathological tissue of the Barrett pathology A. This operation is enabled by the particular feature of any of the embodiments shown in FIGS. 7A-7D, 8A-8D and 9A-9D, which permits forward motion of the endoscope 1000 while it is radially anchored by balloon 1020.

Figure 10F:
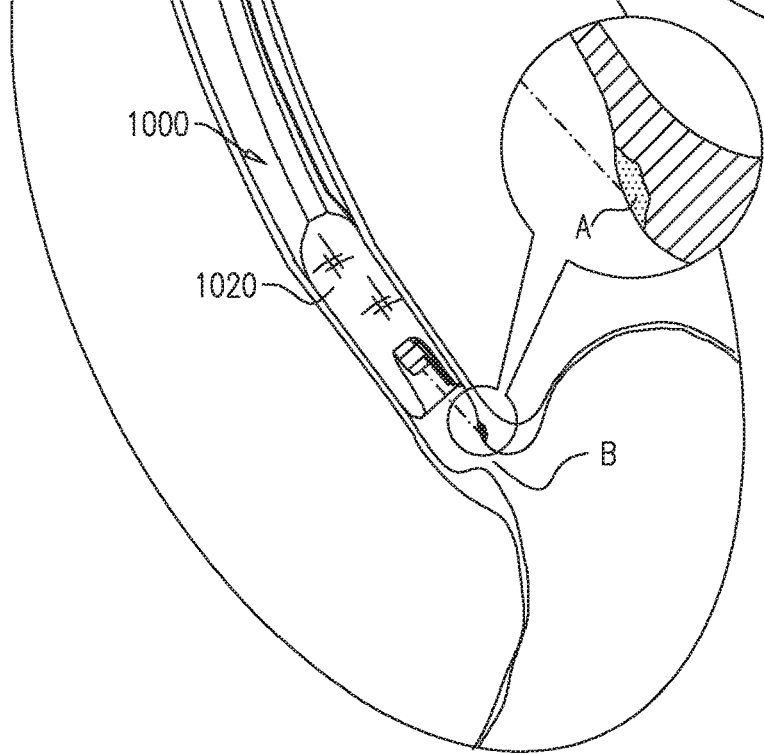

FIG. 10F illustrates subsequent retraction of the endoscope, disengaging the ablation device 1022 from the ablated Barrett pathology A and enabling inspection thereof by the optics on the tip 1024, while endoscope 1000 is radially anchored in the esophagus by balloon 1020. This operation is enabled by the particular feature of any of the embodiments shown in FIGS. 7A-7D, 8A-8D and 9A-9D, which permits rearward motion of the endoscope 1000 while it is radially anchored by balloon 1020.

FIG. 10G illustrates subsequent forward extension of the endoscope such that a forward edge 1028 of the ablation device 1022 engages the ablated Barrett pathology A and peels off the ablated tissue. This operation is done in a carefully controlled manner which is enabled by the anchoring and radial stabilization of the endoscope 1000 by the inflated balloon 1020.

FIG. 10H illustrates subsequent retraction of the endoscope, enabling inspection of the location of treated Barrett pathology A by the optics on the tip 1024.

It is appreciated that the operations shown in FIGS. 10D-10H are all enabled by the particular structure of the embodiments shown in any of FIGS. 7A-7D, 8A-8D and 9A-9D and described hereinabove, whereby the endoscope 1000 may be pushed forwardly and retracted rearwardly in a controlled manner while being radially anchored by the balloon 1020.

Figure 10I:
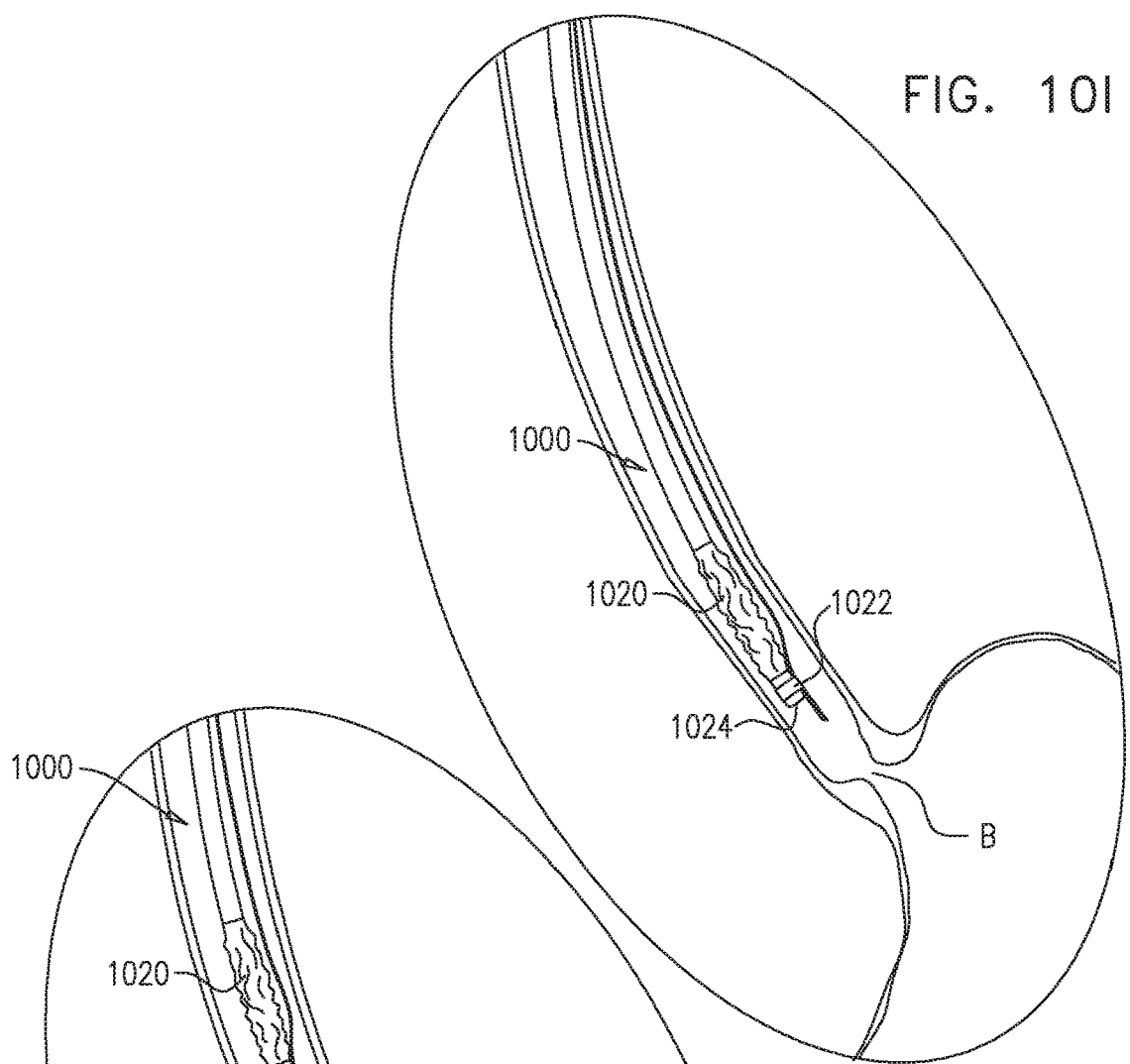

FIG. 10I shows deflation of balloon 1020 and initial withdrawal of endoscope 1000 from the esophagus, following completion of the treatment of the Barrett pathology.

Figure 10J:
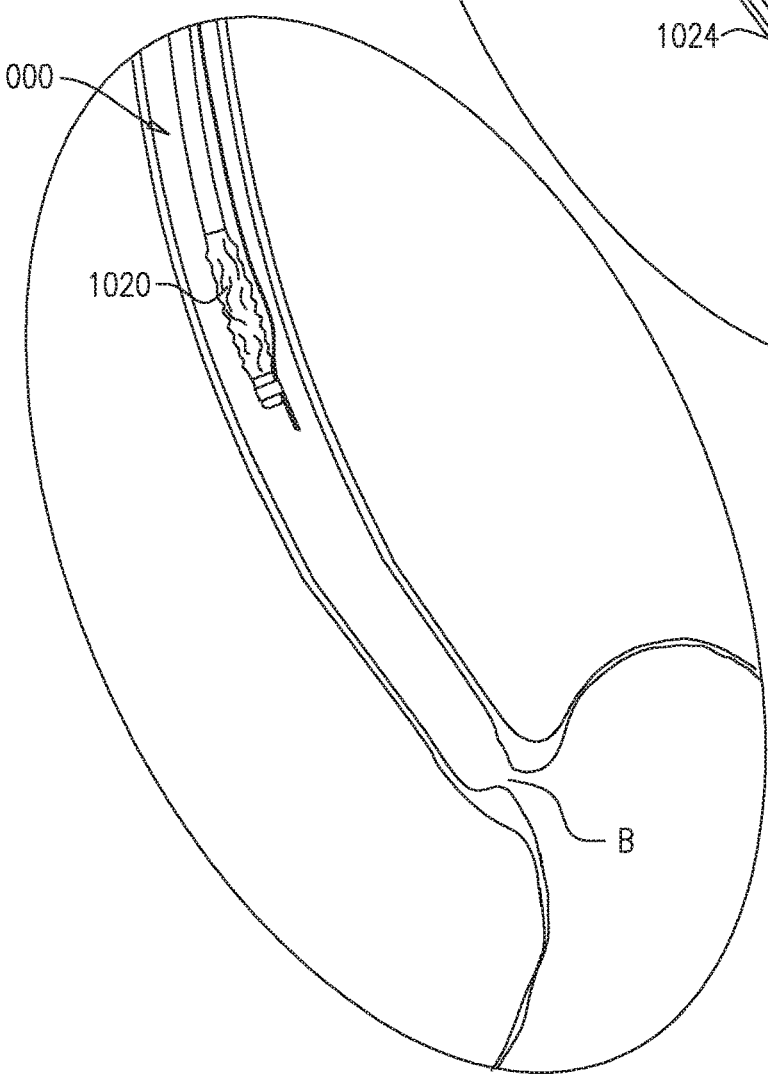

FIG. 10J shows the endoscope 1000 being withdrawn from the esophagus, with balloon 1020 in a deflated state.

It will be appreciated by persons skilled in the art that the present invention is not limited by what has been particularly shown and described hereinabove. Rather the invention includes also combinations and subcombination of various elements described and shown above as well as modifications thereto which would occur to persons skilled in the art upon reading the foregoing and which are not in the prior art.

The invention claimed is:

1. A balloon catheter assembly comprising:
   an elongate catheter tube including a lumen having a first cross-sectional area, said elongate catheter tube comprising an end element having an apertured front face surface, mounted at a forward edge of said elongate catheter tube;
   a wire extending through said lumen and being rotatable relative to said elongate catheter tube; and
   an inflatable balloon mountably associated, at a rearward end thereof, with said elongate catheter tube and mountably associated, at a forward end thereof, with said wire;
   a furling assembly at a rearward portion of said balloon catheter assembly, associated with said elongate catheter tube and with said wire and being operative to rotate said wire about said elongate catheter tube thereby effecting furling of said balloon and rearward axial displacement of said wire relative to said elongate catheter tube;
   said rearward axial displacement having a maximal rearward displacement distance, said maximal rearward displacement distance being a function of the maximal furling allowable by said furling assembly;
   said elongate catheter tube being formed with a plurality of balloon inflation apertures communicating with said lumen, said plurality of balloon inflation apertures having a total aperture cross-sectional area which exceeds said first cross-sectional area of said lumen and including at least two apertures being arranged at different azimuthal locations along said elongate catheter tube underlying said balloon, and
   said balloon being characterized by an inflated state having a ratio of maximum inflated diameter to length of more than 0.4 and a corresponding deflated state wherein at least a first portion of said balloon is capable of being twisted relative to at least a second portion of said balloon, resulting in at least partial blockage of at least one but not all of said plurality of balloon inflation apertures; and
   a limiting element fixedly associated with said wire for limiting retraction of said wire in said elongate catheter tube to a maximal distance H, said maximal distance H being longer than said maximal rearward displacement distance.

2. The balloon catheter assembly according to claim 1 and wherein said wire is retractable into said elongate catheter tube to a maximal predetermined extent.

3. The balloon catheter assembly according to claim 1 and wherein said total aperture cross-sectional area of said plurality of balloon inflation apertures is greater than 1.2 times said first cross-sectional area of said lumen.

4. The balloon catheter assembly according to claim 1 and wherein said total aperture cross-sectional area of said plurality of balloon inflation apertures is greater than 1.5 times said first cross-sectional area of said lumen.

5. The balloon catheter assembly according to claim 1 and wherein said end element is located entirely forwardly of said at least two apertures.

6. The balloon catheter assembly according to claim 1 and also comprising a forward-facing aperture defined in a front face of said elongate catheter tube and having a forward inflation cross-sectional area, said forward facing aperture being in fluid communication with said lumen of said elongate catheter tube.

7. The balloon catheter assembly according to claim 6 and wherein said forward inflation cross-sectional area is between 25%-90% of said first cross-sectional area.

8. A balloon catheter assembly comprising:
an elongate catheter tube including a lumen having a first cross-sectional area and an end element having a forward-facing aperture defined in a front face of said elongate catheter tube, being in fluid communication with said lumen and having a forward inflation cross-sectional area;
a wire extending through said lumen and being rotatable relative to said elongate catheter tube; and
an inflatable balloon mountably associated, at a rearward end thereof, with said elongate catheter tube and mountably associated, at a forward end thereof, with said wire;
a furling assembly at a rearward portion of said balloon catheter assembly, associated with said elongate catheter tube and with said wire and being operative to rotate said wire about said elongate catheter tube thereby effecting furling of said balloon and rearward axial displacement of said wire relative to said elongate catheter tube;
said rearward axial displacement having a maximal rearward displacement distance, said maximal rearward displacement distance being a function of the maximal furling allowable by said furling assembly;
said elongate catheter tube being formed with a plurality of balloon inflation side apertures formed in said elongate catheter tube underlying said balloon and communicating with said lumen, said plurality of balloon inflation side apertures having a total aperture cross-sectional area which exceeds said forward inflation cross-sectional area and including at least two side apertures being arranged at different azimuthal locations along said elongate catheter tube underlying said balloon, and
said balloon being characterized by an inflated state having a ratio of maximum inflated diameter to length of more than 0.4 and a corresponding deflated state wherein at least a first portion of said balloon is capable of being twisted relative to at least a second portion of said balloon, resulting in at least partial blockage of at least one but not all of said plurality of balloon inflation side apertures; and
a limiting element fixedly associated with said wire for limiting retraction of said wire in said elongate catheter tube to a maximal distance H, said maximal distance H being longer than said maximal rearward displacement distance.

9. The balloon catheter assembly according to claim 8 and wherein said wire is retractable into said elongate catheter tube to a maximal predetermined extent.

10. The balloon catheter assembly according to claim 8 and wherein said total aperture cross-sectional area of said plurality of balloon inflation side apertures is greater than 1.3 times said forward inflation cross-sectional area.

11. The balloon catheter assembly according to claim 8 and wherein said end element is located entirely forwardly of said at least two side apertures.

12. The balloon catheter assembly according to claim 8 and wherein said forward inflation cross-sectional area is between 25%-90% of said first cross-sectional area.

* * * * *